(12) United States Patent
Nelson et al.

(10) Patent No.: US 6,448,039 B1
(45) Date of Patent: Sep. 10, 2002

(54) ENHANCER SEQUENCES FOR LATE T CELL EXPRESSED GENES

(75) Inventors: Peter J. Nelson, Munich (DE); Alan M. Krensky, Stanford; Benjamin D. Ortiz, San Francisco, both of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/341,007

(22) PCT Filed: Jun. 14, 1996

(86) PCT No.: PCT/US96/10429

§ 371 (c)(1),
(2), (4) Date: Jun. 30, 1999

(87) PCT Pub. No.: WO97/00266

PCT Pub. Date: Jan. 3, 1997

Related U.S. Application Data

(60) Provisional application No. 60/000,274, filed on Jun. 16, 1995, and provisional application No. 60/014,865, filed on Apr. 4, 1996.

(51) Int. Cl.[7] .......................... C07H 21/04; C12P 21/00
(52) U.S. Cl. .................. 435/69.1; 435/70.1; 435/320.1; 536/24.1
(58) Field of Search .................... 435/320.1, 69.1, 435/70.1, 455; 536/24.1

(56) References Cited

U.S. PATENT DOCUMENTS 5,633,139 A * 5/1997 Prince et al. .................. 435/6
5,824,788 A * 10/1998 Cesbron et al. ............ 536/23.7

FOREIGN PATENT DOCUMENTS

WO    WO 93/25689    * 12/1993

OTHER PUBLICATIONS

Moriuchi et al. 1997. Journal of Immunology 158: 3483–3491.*
Danoff et al., "Cloning, Genomic Organization, and Chromosomal Localization of the Scya5 Gene Encoding the Murine Chemokine RANTES," The Journal of Immunology, (Feb. 1, 1994), vol. 152, No. 3:1182–1189.
Nelson, et al., "Genomic Organization and Transcriptional Regulation of the RANTES Chemokine Gene," The Journal of Immunology, (Sep. 1, 1993), vol. 151, No. 5:2601–2612.
Pattison, et al., "RANTES Chemokine Expression in Cell-Mediated Transplant Rejection of the Kidney," The Lancet, (Jan. 22, 1994), vol. 343:209–211.
Schall, et al., "A Human T Cell–Specific Molecule is a Member of a New Gene Family," The Journal of Immunology, (Aug. 1, 1998), vol. 141, No. 3:1018–1025.

* cited by examiner

Primary Examiner—Remy Yucel
Assistant Examiner—Bronwen M. Loeb
(74) Attorney, Agent, or Firm—Bret E. Field; Paula A. Borden; Bozicevic, Field & Francis, LLP

(57) ABSTRACT

The present invention provides elements derived from a human RANTES promoter that induce expression of a heterologous coding sequence. The invention further provides expression vectors comprising the elements, and host cells comprising the expression vectors. The invention further provides methods of inducing the expression of a heterologous protein in a host.

11 Claims, 10 Drawing Sheets

```
                    SITE R(A)           SITE R(B)
HUMAN    CTTGGTTGCTATTTTGGAAACTCCCCTTAGGGGATGCCCCTCAACTG---CCCTATAAA
         |||||  || || |||||||||||  ||    ||   ||   |||   |||||||||
MURINE   TTTGGTGTCTTTTGTGGAAACTCCCC-AAG-TCCTGGGGCTACCCTGGCTCCCTATAAA
```

```
            *    * *      *
Human:  GATGAGAGAGCAGT
        | |    | | |  | | | | |
Murine: GACTGGAGGGCAGT
```

ENHANCER SEQUENCES FOR LATE T CELL EXPRESSED GENES

The present application claims priority from provisional application U.S. Serial No. 60/000,274, filed on Jun. 16, 1995, and provisional application U.S. Serial No. 60/014, 865, filed on Apr. 4, 1996, both of which are incorporated by reference.

GOVERNMENT RIGHTS

The work disclosed herein was supported by the National Institutes of Health Grant number DK35008. The United States government may have rights in this invention.

TECHNICAL FIELD

The field of this invention concerns isolated nucleic acid sequences that functions as a transcription enhancer elements for heterologous promoters and methods for using it to identify potential compounds that inhibit expression of native RANTES gene product.

BACKGROUND OF THE INVENTION

In humans, inflammatory processes are orchestrated in part by a family of soluble mediators called chemokines. One branch of this gene family, the "CC or $\alpha$ chemokines", includes RANTES, I-309, the monocyte chemotactic proteins MCP-1, MCP-2, MCP-3 and MCP-4 and the macrophage inflammatory proteins MIP-1$\alpha$ and MIP-1$\beta$. The CC chemokines are pro-inflammatory agents that function as potent and highly selective chemoattractants for specific subsets of hematopoietic cells. MIP-1$\beta$ is a chemoattractant for naive helper T cells and MIP-1$\alpha$ attracts cytotoxic T cells and B lymphocytes, while I-309, MCP-1, MCP-2 and MCP-3 are selective for monocytes. RANTES is chemotactic for monocytes, eosinophils, natural killer cells and the "memory" population (CD45RO$^+$) of T lymphocytes. RANTES is released from activated platelets and activates basophils to release histamine.

These multiple activities suggest a role for RANTES in both acute and chronic inflammatory processes. Indeed, high concentrations of RANTES have recently been implicated in the control of the human immunodeficiency virus.

RANTES is expressed as an immediate early gene (6–20 hours) by TNF$\alpha$ stimulated renal tubular epithelium and mesangial cells, TNF$\alpha$ and IL-1$\beta$ activated synovial fibroblasts, and lipopolysaccharide induced monocytes. By contrast, RANTES is expressed in T cells "late" (3–5 days) following activation by antigen or mitogen. This "late" expression of RANTES by T cells is coincident with the development of T cell effector function, including the expression of perforin and granzymes by cytotoxic T lymphocytes. This pattern of expression is in marked contrast to the immediate early expression (6–20 hours) found for other T cell expressed cytokines, such as IL-2, IL-3, IL-4, IL-5, IL-6, and $\gamma$IFN or the chemokines I-309, MIP-1$\alpha$, and MIP-1$\beta$.

A general model has been proposed for the pivotal role of RANTES in the induction, amplification and propagation of an inflammatory response. In this scheme, RANTES and other chemokines are induced rapidly within an inflammatory site and bind to the endothelium, where they attract monocytes and T cells by haptotactic mechanisms. In combination with the induced expression of specific integrin and immunoglobulin superfamily members, chemokines lead to mononuclear cell extravasation. The infiltrating cells then follow a haptotactic/chemotactic trail of chemokines into the interstitium. Within days, T lymphocytes, attracted to the inflammatory site, encounter antigen, become activated, differentiate, and strongly upregulate RANTES protein expression. This production of RANTES by T cells then amplifies and propagates the inflammatory response.

Understanding the transcriptional control of an early lymphokine, interleukin-2, has proven a powerful probe into the mechanism of action of the most potent immunosuppressive drugs in clinical use, cyclosporine and FK506. This information has lead to the development of new drugs and the elucidation of pathways involved in the early stages of T cell activation. Understanding the transcriptional control of the late expressed cytokine, RANTES, may similarly provide insight into the molecular pathways involved in later stages of T cell differentiation and lead to the development of novel immunotherapeutics.

The transcriptional machinery controlling RANTES expression differs among the various tissue types capable of expressing this pro-inflammatory cytokine. The large number of potential consensus transcription factor binding sites found within the immediate upstream region of RANTES is unusual and corroborates the multiple points of control of RANTES expression indicated by functional analyses with reporter genes. This complex system for transcriptional control of RANTES expression, with both early and late kinetics in a variety of different tissue types, indicates that diverse activation signals can give rise to a single common pathway of RANTES release, which in turn leads to the attraction of effector cells into an inflammatory site. This single common pathway, therefore, represents an important potential target for inhibition of the inflammatory response.

This invention provides methods for readily identifying compounds that inhibit RANTES expression in T lymphocytes. These compounds can then be used to control undesired inflammatory responses.

RELEVANT LITERATURE

For a general introduction to RANTES, see Schall, *Cytokine* 3:165 (1992), Schall, et al., *J. Immunol.* 141:1018 (1988) and Nelson, et al., *J. Immunol.* 151:2601 (1993). Wiedermann, et al., *Current Biol.* 3:735 (1993) and Pattison, et al., *Lancet* 343:209 (1994) detail the pivotal role of RANTES in the induction, amplification and propagation of an inflammatory response. And, Nelson, et al., *J. Immunol.* 151:2601 (1993) describes the genomic organization and transcriptional regulation of the human RANTES gene. Baldwin and Sharp, *Proc. Nat. Acad. Sci.* 85:723 (1988) and Baeuerle and Henkel, *Annu. Rev. Immunol.* 12:141 (1994) describe the function and activation of NF-$\kappa$B. Danoff, et al., *J. Immunol.* 152:1182 (1994) describes the murine RANTES.

SUMMARY OF THE INVENTION

This invention is based on the discovery of nucleic acid sequences present in the human RANTES promoter that mediate upregulation of the RANTES gene late in the T cell developmental pathway.

The present disclosure provides an isolated nucleic acid sequence consisting essentially of the sequence of SEQ ID NO:1, or an isolated nucleic acid sequence consisting essentially of the sequence of SEQ ID NO:2, or an isolated nucleic acid sequence consisting essentially of the sequence of SEQ ID NO:3, or an isolated nucleic acid sequence consisting essentially of the sequence of SEQ ID NO:4, or an isolated nucleic acid sequence consisting essentially of the sequence of SEQ ID NO:5.

In one embodiment, the invention provides an isolated nucleic acid sequence the human RANTES enhancer element R(A) (SEQ ID NO:2), said sequence defined by its ability to inducibly express a gene when positioned upstream of the CAAT and TATA boxes of a minimal promoter with the promoter operably linked to the gene to form an expression cassette where the expression cassette is transfected into an activated peripheral blood lymphocyte cell which has been contacted with an amount of anti-CD3 antibody sufficient to induce the expression of the gene with the proviso that the nucleic acid sequence is not operably linked to the RANTES gene product nor to the native RANTES promoter sequences. This R(A) element can be operably linked to a heterologous gene. It can be positioned downstream of a CAAT box and upstream of a TATA box and further separated from said TATA box by a functional NFκB binding site. The NFκB binding site can be the native RANTES NFκB site which has been rendered non-functional.

The R(A) element can also be combined with additional transcriptional elements to form an artificial RANTES promoter. Three elements that can be operably linked to the R(A) element are: (1) the R(C) binding site which is SEQ ID NO:3 corresponding to −182 to −169 of the human Rantes promoter; (2) the Region "C" sequence corresponding to −195 to −144 of the human Rantes promoter which is SEQ ID NO:4; or (3) the Region E sequence corresponding to −115 to −91 of the human Rantes promoter which is SEQ ID NO:5.

This R(A) element as well as the above-identified transcriptional regions can be recombined with additional nucleic acid sequence to form a vector. The R(A) element can be operably linked to a DNA sequence which encodes a heterologous protein. The heterologous protein can be selected from the group consisting of: hormones, viral capsid proteins, bacterial enzymes and mammalian enzymes. The vector containing the R(A) element recombined with additional nucleic acid sequence can be transfected into a host cell. Said host cell can be a mammalian cell competent to express the binding elements needed to induce expression of the heterologous protein. Said cell can be activated peripheral blood lymphocytes or T cell tumor line Hut78.

Methods for inducing the expression of heterologous proteins and for detecting inhibitors of RANTES production are also provided by this invention.

This invention provides a method for inducing the expression of a heterologous protein in a host cell having nucleic acid sequence encoding the heterologous protein wherein said nucleic acid sequence is operably linked to a promoter comprising the R(A) enhancer element derived from the nucleic acid sequence encoding the human RANTES protein and further defined by (a) the ability to inducibly express a gene when operably linked to a gene forming an expression cassette and (b) the ability of the expression cassette when transfected into a peripheral blood lymphocyte in the presence of anti-CD3 antibody to induce the expression of the gene, with the proviso that the nucleic acid is not operably linked to the RANTES gene product nor to the native NFκB binding element of the RANTES gene, said method comprises: (i) transfecting the host cell with the expression cassette having nucleic acid sequence encoding the heterologous protein; and (ii) inducing the expression of the heterologous protein.

Other methods of inducing the expression of heterologous proteins include those that have SEQ ID NO:2 for the R(A) element. They also include those where said host cell is selected from the group consisting of activated peripheral blood lymphocytes and T cell tumor line Hut78, or said host cell is transfected with a plasmid. Additionally, said heterologous protein can be selected from the group consisting of: hormones, viral capsid proteins, bacterial enzymes and mammalian enzymes. These methods further include those where said nucleic acid sequence is transfected into a human host cell or where the host cell is induced to express a heterologous gene by contacting the cell with an appropriate activator in an amount sufficient to induce expression of the gene.

To obtain optimal control of expression of the RANTES R(A) element, one can add any of the above transcriptional elements.

This invention also provides a method for detecting inhibitors of RANTES production by inducing the expression of a heterologous protein in a host cell having the nucleic acid sequence encoding the heterologous protein wherein said nucleic acid sequence is operably linked to a promoter comprising the R(A) element from the promoter of the gene encoding the human RANTES protein, wherein the promoter does not include the other native cis binding sites of the RANTES gene and is further defined by (a) the ability to inducibly express a gene when operably linked to a gene forming an expression cassette and (b) the ability of the expression cassette when transfected into a peripheral blood lymphocyte in the presence of anti-CD3 antibody to induce the expression of the gene, said method comprises: (i) transfecting the host cell with the expression cassette having nucleic acid sequence encoding the heterologous protein; (ii) choosing a composition of matter that potentially has inhibitory effect on RANTES expression; (iii) inducing the expression of the heterologous protein in the presence of said potential inhibitor; and (iv) assaying for decreases in the level of expression. The above described transcriptional elements, i.e., the C Region, the C binding site and the E Region may all be combined with the R(A) element to ensure that the inhibitor has the desired specificity.

DEFINITIONS

Figure 1:
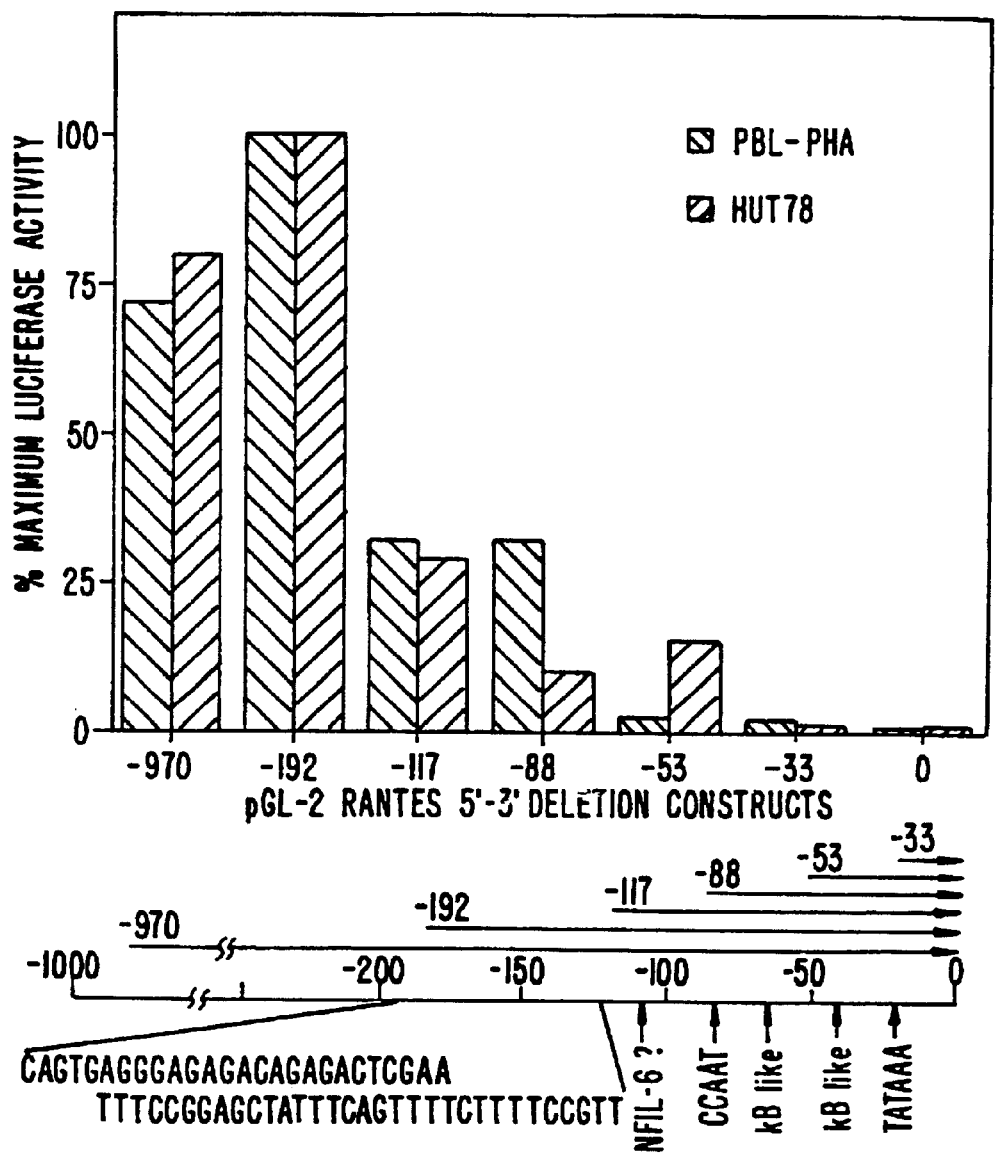
FIG. 1: A series of 5' to 3' deletions of the RANTES promoter were fused to a luciferase reporter gene and transiently transfected via electroporation into either Hut78 cells or day 1.5 PHA activated PBL cells and tested for reporter gene activity 36 hours later. Results are average values of quadruplicates for Hut78 cells or triplicates for PBL cells and are presented as percent maximum activity relative to the −192 construct. (Maximum values (×1000) for Hut78 515+/−120 for PBL 1165 +/−414.). The map demonstrates the relative position of various elements in the RANTES promoter previously described in Nelson, et al. *J Immunol.* 151:2602 (1993), and showing the sequence of −158 to −101 of the RANTES promoter (SEQ ID NO:20).

The term "isolated" when used in relation to a nucleic acid or a protein refers to a nucleic acid or protein that is identified and separated from at least one containment nucleic acid or protein with which it is ordinarily associated in its natural source.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the coding sequence. A ribosome binding site is operably linked to a coding sequence if it is positioned so as to permit translation of the coding sequence. Linking is accomplished by ligation at convenient restriction sites. If such sites do not exist, synthetic oligonucleotide adaptors or linkers are used in accord with conventional practice.

"Promoters" are untranslated DNA sequences located upstream from the start codon of a structural gene (generally within about 100 to 1000 bp) that control the transcription of genes. Promoters typically fall into two classes, inducible and constitutive. Inducible promoters initiate increased levels of transcription from DNA under their control in response to some change in environmental conditions; e.g., the presence or absence of a nutrient or a change in temperature. Constitutive promoters produce a constant level of transcription from DNA under their control when exposed to their native conditions.

A "TATA" box, an upstream promoter element, is the DNA sequence TATAAA that is generally located −25 to −30 relative to the RNA start site. This sequence is part of the promoter sequence of eukaryotic genes and binds transcription factor IID (TFIID). RNA polymerase recognizes the TFIID-TATA protein-DNA complex. The TATA box sequence is critical both for promoter activity and for determining the exact point of RNA chain initiation.

The "CAAT" box is an upstream promoter element generally located at −75 to −80 relative to the RNA start site. It influences the frequency of initiation, most likely by acting directly on the basal transcription factors to enhance their assembly into an initiation complex. The sequences between the CAAT and TATA elements are irrelevant and the distance between them is flexible. The separation between the CAAT and TATA elements can usually be changed by 10 to 30 base pairs before rendering them inoperable.

An "enhancer" element is a regulatory DNA sequence whose presence is associated with increased transcription of coding sequences associated with the enhancer element, either by initiating transcription from a promoter operably linked to the enhancer or by providing binding sites for gene regulatory proteins that increase transcription of a minimal promoter. Because enhancer activity falls off progressively with distance, enhancers usually function best when located close to promoter sequences. Enhancers generally function regardless of their orientation relative to promoter sequences.

A "minimal promoter" is a promoter sequence containing only the CAAT and TATA boxes without any enhancer elements.

"Transfection" refers to the taking up of an expression vector by a host cell whether or not any coding sequences are expressed. Numerous methods of transfection are known to the ordinary person skilled in the art; for example, $CaPO_4$ and electroporation. A host cell has been successfully "transfected" when any indication of the operation of this vector occurs within the host cell.

"Hut78" is a cell line derived from a cutaneous T cell lymphoma that expresses a "late" T cell phenotype; i.e., constitutively expresses IL-2 receptor, IL-2 and RANTES.

The "RANTES gene" is a member of a large supergene family of pro-inflammatory cytokines called CC chemokines that play a fundamental role in the inflammatory process. Schall, et al., *J. Immunol.* 141:1018 (1988). The RANTES gene spans approximately 7.1 kb and is located on the long arm of chromosome 17.

The "RANTES gene product" is a protein which causes the release of histamine from basophils and is a chemoattractant for $CD45RO/CD4^+$ memory T lymphocytes, monocytes, basophils, eosinophils and natural killer cells.

The "native RANTES promoter sequence" consists of an approximately 1 kb DNA region representing the immediate 5' upstream region and 5' untranslated region of the RANTES gene.

"NF-κB" is a nuclear factor that binds to KB consensus DNA sequences. One such κB consensus DNA sequence, 5' to 3', is GGGACTTTCC SEQ ID NO:9).

The term "heterologous" refers to a DNA sequence not ordinarily found in a given gene.

The phrase "Inducing the expression of a nucleic acid" means that a cell that contains a nucleic acid commences or upregulates the transcription of that nucleic acid in response to an environmental signal, typically exposure to a substance that activates the cell to differentiate.

A "nuclear factor" is a substance present in the nucleus of the cell that bonds to specific regulatory nucleic acid sequences that modulate the expression of a given gene. The nuclear factor may, by way of example, be a protein, nucleic acid, or a combination thereof.

The phrases "modulator of RANTES production" and "modulatory" refers to an agent that increases or decreases RANTES expression by binding to the RANTES promoter, usually at a specific sequence, and inducing upregulation or downregulation of RANTES gene transcription. A modulator of RANTES production "operates through the R(A,C or E) site" (1) if it binds directly to the site and modulates RANTES production by virtue of binding, (2) if it induces or inhibits the synthesis, degradation or activation of a nuclear factor that itself binds to the site, or (3) it competes with binding of a nuclear factor to the site.

The term "recombinant" or "engineered" when used with reference to a nucleic acid indicates that the nucleic acid has been altered as compared to the naturally occurring nucleic acid or protein. The term "recombinant" or "engineered" when used with reference to a protein indicates that the nucleic acid that encodes the protein has been altered as compared to the naturally occurring nucleic acid. The alteration encompasses deletions, insertion and substitutions in the sequence of the naturally occurring nucleic acid, and also ligation of naturally occurring nucleic acids in combinations not normally found in nature.

The term "recombinant" or "engineered" when used with reference to a cell indicates that the cell replicates or expresses a recombinant nucleic acid or expresses a peptide or protein encoded by a recombinant nucleic acid, whose origin is exogenous to the cell. Recombinant cells can express nucleic acids that are not found within the native (nonrecombinant) cell. Recombinant cells can also express nucleic acids found in the native cell wherein the nucleic acids are re-introduced into the cell by artificial means.

The term "non-functional" refers to a DNA sequence which has been mutated, such as by base pair substitution or addition, such that its native biological characteristics are no longer recognizable. For example, the DNA sequence, κB, is a binding element for the NF-κB protein. If substantial mutations are created such that the κB sequence no longer resembles the recognized consensus, then it will no longer bind NF-κB protein and, therefore, it will have been rendered non-functional.

The phrase "consisting essentially of" means the DNA sequence in question can have base pair substitutions, or extra base pairs added to either the 5' or the 3' end, and still be functionally equivalent to the DNA element described.

DETAILED DESCRIPTION

A. Introduction

The RANTES chemokine is a potent pro-inflammatory cytokine, which has been identified as a major HIV-suppressive factor produced by T cells.

We have identified (in the promoter region of the RANTES gene) a novel enhancer element—designated the R(A) sequence—which is critical for promoter activity in both the T cell tumor line Hut78 and in PHA activated peripheral blood lymphocytes (PBL). This enhancer element binds not only known Rel family members (including p50 homodimers and p50–p65 heterodimers) but also non-Rel factors newly upregulated in PBL cells by day 3–5 following activation. Unlike the Rel proteins, which are expressed in various different tissue cells, these late-expressed factors correlate precisely with the induction of RANTES message. These novel proteins—designated the R(A)FLAT complex—are likely responsible for the temporal regulation of RANTES in peripheral blood T cells and are a component of the transcriptional regulatory machinery newly expressed in late-stage T cell development.

In addition to the critical R(A) region we have also identified additional regions—the R(C) and R(E) regions—which assist in the expression of RANTES. When deleted, the R(C) region diminishes the ability of R(A) to drive expression by about 54% and the R(E) by about 66% compared to the wild type promoter.

The newly identified enhancer sequences can be obtained in a variety of ways. Once obtained, these sequences have two primary uses. First, they can be used an inducible enhancer elements when operably linked to a heterologous promoter. In this fashion, any heterologous gene can be inducibly expressed in Hut78 cells or activated PBL cells with "late" kinetics. More importantly, the R(A) sequence can be used to screen for compounds that can inhibit expression of native RANTES gene product in T lymphocytes. In combination, the R(A) and R(C) and R(E) elements permit an increased degree of control and aid in the identification of specific inhibitors of RANTES expression or of expression of heterologous genes placed under the control of these elements.

B. The Rantes Transcriptional Elements and how to Obtain Them

The R(A) sequence, in 5' to 3' order, is GCTATTTTG-GAAACTCCCCTTAG (SEQ ID NO:2) which is the native RANTES sequence found at −71 to −49 relative to the RANTES transcription start site. In the native RANTES gene, this sequence is located between the CAT and TATA boxes. Binding site C is internal to region C and has SEQ ID NO:3 GATGAGAGAGCAGT which corresponds to −182 to −169 relative to the RANTES transcriptional start site. Region C has SEQ ID NO:4 GAGCTCACTCTAGAT-GAGAGAGCAGTGAGGGAGAGACA-GAGACTCGAATTT and corresponds to −195 to −144 relative to the RANTES transcriptional start site. Region E has SEQ ID NO:5 TTTGTGCAATTTCACTTATGATACC and corresponds to −115 to −91 relative to the RANTES transcriptional start site. All sequences are 5' to 3'.

Those skilled in the art will recognize that a number of bases in the R(A) sequence can be substituted without detrimentally affecting its function. For example, a T residue can be substituted for the first A residue from the 5' end. Similarly, an A residue can be substituted for the fourth T residue in the string of four T residues immediately downstream of the just mentioned first A residue. The GGAAACTCCCC (SEQ ID NO:19) portion of the R(A) sequence is a κB-like sequence which can also be altered so long as the changes stay consistent with the κB recognized consensus sequence as described by Baeuerle and Henkel, *Ann. Rev. Immunol.* 12:141 (1994). The two guanine residues within this stretch are critical for transcription factor binding. No more than any two bases can be changed.

One can obtain the above sequences by many methods. The more common include chemical synthesis by known methods such as phosphotriester, phosphite, or phosphoramidite chemistry, using solid phase techniques such as described in EP 266,032 published May 4, 1988, or deoxynucleoside H-phosphonate intermediates as described by Froehler et at., *Nucl. Acids Res.*, 14: 5399–5407 (1986).

One can also amplify the above sequences directly from the genomic RANTES DNA using the polymerase chain reaction (PCR) as described in U.S. Pat. No. 4,683,195 issued Jul. 28, 1987. For example, for R(A), sequence information from the ends of the stretch of interest (the native RANTES base pairs −71 to −49 as described previously) or beyond must be available so that oligonucleotide primers can be designed. These primers will point towards one another and will be identical or similar in sequence to opposite strands of the template to be amplified. The 5' terminal nucleotides of the two primers will coincide with the ends of the amplified material.

Finally, the R(A) oligonucleotide sequence (whether double or single stranded) can be readily synthesized by any number of commercial suppliers such as Genset (San Diego, Calif.) or Clontech (Palo Alto, Calif.). Commercial suppliers, as well as anyone synthesizing or PCR amplifying the sequence themselves, can create the sequences with particular requested overhangs to match any particular cloning needs.

C. Using the R(A) Sequence as an Inducible Enhancer Element to Heterologous Promoters As demonstrated by Example 2, the R(A) sequence can be used as an inducible enhancer element when operably linked to heterologous promoters. In Example 2, the R(A) sequence was joined to an SV40 minimal promoter which drives the transcription of the luciferase gene. The vector containing these sequences was then transfected into Hut78 cells and also activated PBL cells. Transfection into mammalian cells is generally carried out by the calcium phosphate precipitation method as described by Graham and Van der Eb, *Virology*, 52: 546 (1978). However, other methods for introducing DNA into cells such as nuclear injection, electroporation (used in Example 2), or protoplast fusion are also suitably used. An increase in luciferase activity was observed in those constructs that had the R(A) enhancer element as opposed to those that did not.

While it is critical that promoter sequences be in the proper orientation relative to the gene sequences to be transcribed, the orientation of the R(A) enhancer element is not critical. It is preferable that the R(A) element be located immediately upstream of the desired promoter, but enhancer elements can generally be located anywhere on the vector and still have an enhancing effect. However, the amount of increased activity will usually diminish with distance. Additionally, two or more copies of the R(A) sequence can be operably linked one after the other to produce an even greater increase in promoter activity.

A promoter driving a gene of interest can be expressed in T lymphocytes using the R(A) sequence. Some candidate promoters include the SV40, thymidine kinase and IL-2 promoters among many others. The type of cells in which the gene construct is expressed controls the inducement of the enhancer. The transcription factors necessary to induce the native RANTES promoter in T lymphocytes bind to the R(A) sequence. These factors are expressed in Hut78 cells or in activated PBL cells. Hut78 cells are preferable when constitutive R(A) enhancer activity is warranted since Hut78 cells express a "late" T cell phenotype and constitutively produce the necessary transcription binding factors. Likewise, any other cell type with a "late" T cell phenotype can be used as an expression host.

Similarly, one can control induction of the R(A) enhancer by using peripheral blood lymphocytes as the expression host. Since the necessary transcription binding factors are present only in activated PBL cells, the R(A) enhancer will be dormant until activation. One can activate PBL cells in a number of ways. One of the more common ways to activate all T lymphocytes in a PBL population is by mitogenic stimulation through exposing the cells to a mitogen such as phytohemagglutinin-m. Alternatively, one way to activate all T lymphocytes is to expose the PBL cells to an anti-CD3 antibody, such as the commercially available OKT3 antibody, which activates all T cell receptors. Another possible activation method consists of activating a specific subset of T lymphocytes by exposing the cells to the particular antigen for the particular T cell receptor of that desired subset of T lymphocytes.

In short, a desired promoter/gene construct can be enhanced when operably linked to the R(A) sequence so long as Hut78 or activated peripheral blood lymphocyte nuclear extract is present.

D. Using the R(A) Sequence to Identify RANTES Gene Product Inhibitors

The most beneficial characteristic of the R(A) sequence is its ability to be used as an identifier of inhibitors of native RANTES gene product expression. RANTES production correlates with late T cell effector function. Late T cell effector function has been linked to T cell mediated autoimmune diseases such as multiple sclerosis, rheumatoid arthritis and juvenile diabetes, as well as common allergies and asthma. Inhibitors of RANTES production could possibly alleviate some or all of the symptoms of these diseases.

To test any possible compound for its effect on native RANTES gene product expression, one can perform any of the three assays described in Example 3. The simplest and fastest way to identify potential inhibitors would be to use the luciferase gene fusion assay. In that assay, the test compound can be added directly to the cell growth media following transfection. The results can then be compared to the results obtained from a control run containing no extra compounds. If a compound causes a drop, preferably a significant drop, in luciferase activity, then the compound will likewise inhibit the expression of native RANTES gene product.

Ideally, any compounds that decrease the luciferase activity should then be tested in the DNAse I footprinting and the EMSA as described in Example 3. Once again, test compounds can be added directly to the growth media and incubated for a sufficient amount of time to have an effect. Generally, a few days of exposure to the test compound should be sufficient for the compound to either inhibit expression of one of the transcription factors necessary for binding to the R(A) sequence, or directly block the binding at the R(A) site. The assays are described in Example 3. An inhibitory compound will produce no bands in the DNAse footprinting assay and a lessening or complete disappearance of bands one and two in the EMSA.

It is important to note that any promoter/reporter gene fusion assay system can be used to test for inhibitors so long as the construct includes the R(A) enhancer element. The only critical step is to transfect the construct into a cell type, such as Hut78 or activated PBL cells, that actively produces the normal transcription factors necessary for native RANTES gene expression. Other cells that express native RANTS production include the erythroleukemic cell line HEL, the rhabdomyosarcoma cell line RD, TNFα stimulated renal tubular epithelium, TNFα stimulated renal tubular epithelium mesangial cells, TNFα activated synovial fibroblasts, IL-1β activated synovial fibroblasts and lipopolysaccharide induced monocytes. The transfection must be done both in the presence of the test compound and separately without the test compound so that relative results can be measured. The compounds that show inhibitory effect can then be tested against each other to ascertain those with the highest inhibitory effect.

E. Combinations of the R(A) with R(C) or R(E) Sequences

Using the above-described techniques, the R(C) and R(E) sequences and the R(A) sequence can both be simultaneously operably linked to a promoter (especially a minimal promoter) which is operably linked to a coding sequence (e.g., a reporter gene, or the RANTES gene). The resulting expression cassette is regulated by nuclear factors that bind to these sites. A full description of the R(C) and R(E) elements can be found in Ortiz et al., *Mol. Cel. Biol.* 16:202–210 (1996).

1. Using the R(C) Sequence to Identify RANTES Gene Product Inhibitors

A beneficial property of the R(C) sequence is its use to identify inhibitors of native RANTES gene product expression. Late T cell effector function has been lined to T cell mediated autoimmune diseases such as multiple sclerosis, rheumatoid arthritis and juvenile diabetes, as well as common allergies and asthma. Inhibitors of RANTES production could possibly alleviate some or all of the symptoms of these diseases.

To test any possible compound for its effect on native RANTES gene product expression, one can perform any of the assays described in the examples below. The simplest and fastest way to identify potential inhibitors would be to use a known assay, such as the luciferase gene fusion assay. In that assay, the test compound is added directly to the cell growth media following transfection with a vector in which the luciferase gene is operably linked to a RANTES promoter that comprises the R(A) and R(C) site. The results can then be compared to the results obtained from a control run containing no extra compounds. If, for example, a compound causes a drop, preferably a drop of 50% or greater, in luciferase activity, then the compound likewise inhibits the expression of native RANTES gene product.

Ideally, any compounds that decrease luciferase activity should be tested in the DNAse I footprinting and the EMSA as described in the examples below. Once again, test compounds can be added directly to the growth media and incubated for a sufficient amount of time to have an effect. Generally, a few days of exposure to the test compound should be sufficient for the compound to either inhibit expression of one of the transcription factors necessary for binding to the R(C) sequence, or directly block the binding at the R(C) site. The assays are amply described in the examples below. An inhibitory compound will simply produce no bands in the DNAse footprinting assay and a lessening or complete disappearance of bands one and two in the EMSA.

It is important to note that any promoter/reporter gene fusion assay system can be used to test for inhibitors so long as the construct includes the R(A) and R(C) enhancer elements. The only critical step is to transfect the construct into a cell type, such as HUT78 or activated PBL cells, that actively produces the normal transcription factors necessary for native RANTES gene expression. Other cells that express native RANTES production include the erythroleukemic cell line HEL, the rhabdomyosarcoma cell line RD, TNFa stimulated renal tubular epithelium, TNFa stimulated renal tubular epithelium mesangial cells, TNFa activated synovial fibroblasts, IL-1b activated synovial fibroblasts and lipopolysaccaride induced monocytes. The transfection must be done both in the presence of the test compound and separately without the test compound so that relative results can be measured. The compounds that show inhibitory effect can then be tested against each other to ascertain those with the highest inhibitory effect.

2. Using the R(C) Sequence as an Inducible Enhancer Element to Heterologous Promoters.

The R(C) sequence can be used as an inducible enhancer element when operably linked to R(A) and heterologous promoters. To this end, the R(A) and R(C) sequence is placed in front of a minimal promoter which drives the transcription of the luciferase gene (e.g., an SV40 minimal promoter). The vector containing these sequences is then transfected into HUT78 cells and also activated PBL cells by known methods.

EXAMPLES

The following examples are provided by way of illustration only and are not intended to limit the invention in any way. Those of skill will readily recognize a variety of noncritical parameters (e.g., vectors, cell lines, reporter genes, sources of nucleic acids) which could be changed or modified, and also other embodiments that are within the scope of the present invention.

MATERIALS AND METHODS

Cells and Cell Lines

HUT78 (ATCC TIB 161), Jurkat (ATCC TIB 152), Burkitt's B-lymphoma cell lines MS (Wright, A., et al, *J. Exp. Med.* 169:1557–1564 (1989)) and Daudi (ATCC CCL 213), PEER ($\lambda\delta$ T cell), and normal peripheral blood lymphocytes (PBL) were cultured and maintained in RPMI 1640 medium (Irvine Scientific, Santa Ana, Calif.) supplemented with 2 mM L-glutamine, 100 U of penicillin G per ml, 100 U of streptomycin per ml, and 10% heat-inactivated fetal calf serum (HyClone Laboratories, Inc., Logan, Utah). YT2C2, a natural killer cell tumor, was cultured as described above, with sodium pyruvate added to a final concentration of 1 mM. Normal human CTL lines were generated and maintained as described in Clayberger et al., *J. Immunol.* 144: 4172–4176. RD (ATCC-CCL 136), a rhabdomyosarcoma, was cultured in RPMI 1640–15% bovine calf serum supplemented with nonessential amino acids and vitamins. Normal dermal fibroblasts were cultured as described previously (Spaete, R. R., et al.,*J. Virol.* 56:135–143 (1985)). SK-HEP-1(ATCC HTB 52), cells were cultured in Dulbecco modified Eagle medium (DMEM) with 10% fetal calf serum, 2 mM L-glutamine, 100 U of penicillin G per ml. and 100 U of streptomycin per ml.

Peripheral blood lymphocytes (PBL) were isolated by Ficoll density gradient centrifugation from buffy coats obtained from healthy blood donors at the Stanford Blood Bank. The viability of isolated PBL was greater than 99% as determined by trypan blue exclusion. PBL cells were then suspended at $2-4\times10^6$ cells/ml in tissue culture medium (RPMI 1640 supplemented with L-glutamine, penicillin, streptomycin and 20% heat inactivated fetal calf serum). Incubation for two hours at 37° C. in 175 cc horizontal flasks (LUX, Naperville, Ill.) reduced adherent cells (monocytes) in each preparation. Nonadherent cells were then transferred to a new 175 cc horizontal flask for subsequent experiments. The PBL cells were activated with 5 $\mu$g/ml T-cell mitogen phytohemagglutinin-P PHA-P (DIFCO, Detroit, Mich.) and incubated at 37° C. for varying lengths of time. Only the nonadherent cells were harvested for experiments. This activated population was greater than 95% T cells as determined by flow cytometry by using a monoclonal antibody to CD3 (OKT3). All cells were cultured in horizontal flasks (LUX, Naperville, Ill.).

Oligonucleotides

Oligonucleotides such as the R(A) and R(C) sequences and mutants thereof are obtained by many methods. The more common is chemical synthesis by known methods such as phosphotriester, phosphite, or phosphoramidite chemistry, using solid phase techniques such as described in EP 266,032 published May 4, 1988, or deoxynucleoside H-phosphonate intermediates as described by Froehler et al., *Nucl. Acids Res.*, 14: 5399–5407 (1986).

Another method is to amplify the desired sequence directly from a natural source. (e.g., genomic RANTES DNA) using the polymerase chain reaction (PCR) as described in U.S. Pat. No. 4,683,195 issued Jul. 28, 1987. Generally, sequence information from either side of the stretch of interest or beyond must be available so that oligonucleotide primers can be designed. These primers will bracket the desired sequence and will be identical or similar in sequence to opposite strands of the template to be amplified. The 5' terminal nucleotides of the two primers will coincide with the ends of the amplified material.

Finally, the desired oligonucleotide sequence (whether double or single stranded) can be readily synthesized and purchased by any number of commercial suppliers such as Genset (San Diego, Calif.) or Clontech (Palo Alto, Calif.). Commercial suppliers, as well as anyone synthesizing or PCRing the sequence themselves, can create the R(C) sequence with particular requested overhangs to match any particular cloning needs.

Reporter Gene Assays

For the reporter gene assays, a nucleic acid containing the promoter sequences to be studies was operably linked to a reporter gene. Nonlimiting examples of reporter genes include the luciferase gene or the $\beta$-galactosidase gene.

The construction of various RANTES promoter luciferase reporter constructs has been previously described. Nelson, P. J., et al., *J. Immunol.* 151:2601–2612 (1993). Luciferase assays were performed using the luciferase assay system kit (Promega) as described previously. Id. It is preferable that the enhancer sequence be located immediately upstream of the desired promoter, but effective enhancer elements can be located at more than one site of the promoter and still have an enhancing effect. However, the amount of increased activity will usually diminish with distance. Additionally, two or more copies of the R(C) sequence can be operably linked one after the other to produce an even greater increase in promoter activity.

$\beta$-Galactosidase assays were performed with an aliquot of transfected cell extracts according to the instructions accompanying the reporter lysis buffer reagent (catalog no. E397A; Promega) with o-nitrophenyl-$\beta$-o-galactopyranoside (ONPG). The results were recorded on a Beckman DU62 spectrophotometer set at a wavelength of 420 nm. All constructs were tested at least in triplicate. Only plasmids prepared at the same time were directly compared in reporter gene assays, and all results reported were confirmed with at least two separate plasmid preparations.

Transfection

Vectors containing the engineered sequences and expression cassettes are transfected into appropriate cells of the invention (HUT78 cells or activated PBL cells), for example, by the calcium phosphate precipitation method as described by Graham and Van der Eb, *Virology*, 52:546 (1978), by electroporation, or by protoplast fusion.

Nuclear Extracts

Nuclear extracts for EMSA and DNAase I footprinting were prepared essentially according to the protocol of Durand, D., et al., *Mol. Cell. Biol.* 8:1715–1724), except 0.2% Nonidet P-40 was used in buffer A to lyse the cells instead of the homogenizer. All subsequent steps were carried out at 4° C. Nuclei were prepared by resuspending the cells in buffer A [10 mM Hepes (pH 7.6), 15 mM potassium chloride (KCl), 2 mM magnesium chloride ($MgCl_2$, 0.1 mM ethylenediaminetetraacetate (EDTA) (pH 8.0), 1 mM dithiothreitol, and 0.1 mM phenylmethylsulfonylfluoride (PMSF)]. After incubation on ice for 15 minutes, the cells were gently pelleted at 900×g and then gently resuspended in five times the original cell pellet volume in buffer A with 0.2% NP40 (Sigma). After five minutes, the cell lysate was pelleted at 2000×g and resuspended in buffer C, containing 25 mM Hepes (pH 7.6), 50 mM KCl, 0.1 mM EDTA, 10% volume to volume glycerol, 1 mM dithiothreitol, and 0.1 mM PMSF. Nuclei were lysed and chromatin-bound DNA precipitated by the addition of 0.3 M ammonium sulfate [$(NH_4)_2SO_4$]. The protein fraction containing nuclear factors was then precipitated with 0.22 g/ml $(NH_4)_2SO_4$]. Resulting extracts were desalted, using a P6DG resin (Bio-Rad, Hercules, Calif.) equilibrated with buffer C, and stored at −80° C. until quantitated and used in the various assays. Extracts were quantitated by the Bradford assay using the Bio-Rad protein assay reagent.

Electrophoretic Mobility Shift Assay (EMSA)

Electrophoretic mobility shift assays are used to characterize nuclear factors which bind DNA. The following describes the normal expected results when no inhibitory compound is present. If a test compound does inhibit the production of native RANTES gene product then the results of these assays will be altered as described.

The electrophoretic mobility shift assay (EMSA) was performed essentially as described previously (Durand, D., et at., *Mol. Cell. Biol.* 8:1715–1724, and Jones et al. *Cell* 42:5593 (1985). Briefly, binding reactions (15 µl final volume) contain 10 mM Tris-HCl (pH 7.5), 80 mM sodium chloride, 1 mM dithiothreitol, 1 mM EDTA, 5% glycerol, 1.5-2 µg of poly(dI • dC), 5 to 10 µg of nuclear extract, and 20,000 cpm (0.1 to 0.5 ng) of the $^{32}$P-end-labeled double-stranded oligonucleotide probe. After incubation for 45–60 min on ice, the protein-DNA complexes were resolved on nondenaturing 5% polyacrylamide gels run in 1X Tris-borate-EDTA (TBE) buffer (Ausubel, F. M., et al., Green Publishing Associates and Wiley-Interscience, New York (1987)).

Oligonucleotides were synthesized by Genset (San Diego, Calif.), with 3' overhangs that could be end labeled by the Klenow fragment as described previously (Ausubel, F. M., et al., Green Publishing Associates and Wiley-Interscience, New York (1987); Durand, D., et al., *Mol. Cell. Biol.* 8:1715–1724).

For cold oligonucleotide competition assays, a 1,000-fold molar excess of unlabeled DNA was added to the binding reaction mixture 15 min into the incubation, and the mixture was further incubated for 30 min at 4° C. prior to gel loading, C/EBP family antisera (α, β, and γ) were purchased (Santa Cruz Biotechology, Santa Cruz, Calif.) and used according to the manufacturer's instructions.

The ets family antisera was a gift (R. Fisher, National Cancer Institute, Frederick, Md.) (Rosen, G. D., et al., *J. Biol. Chem.* 269:15652–15660 (1994)).

DNAse I Footprinting Assay

DNase I footprinting is used to assay for DNA sequences which could be protected from DNase I digestion by nuclear extracts isolated from activated T cells. DNase I footprinting of the minimal RANTES promoter identifies a large region protected by T cell derived nuclear extracts (Nelson et al., 1993 *J. Immunol.* 151:2601) The presence of an inhibitory compound will prevent the activated PBL or HUT78 cell nuclear extract from protecting this region. A negative and positive control run on either side of the test compound will produce adequate points of reference.

DNAse I footprinting is performed using a derivation of the procedures described by Durand et al., *Mol. Cell. Biol.* 8:1715 (1988) and Jones et al., *Cell* 42:5593 (1985). Binding reactions are carried out under the conditions described above for EMSA but scaled up to 50 µl. After binding, using 50 µg nuclear extracts, 50 µl of a 10 mM $MgCl_2$/5 mM $CaCl_2$ solution is added and 2 µl of an appropriate DNAse I (Worthington, Freehold, N.J.) dilution is added and incubated for 1 minute on ice. DNase I digestion is stopped by adding 90 µl of stop buffer (20 mM EDTA, 1% SDS, 0.2 M NaCl). After addition of 20 µg yeast tRNA as carrier, the samples are extracted two times with an equal volume of phenol/chloroform (1:1) and precipitated after adjusting the solution to 0.3 M sodium acetate and 70% ethanol. DNA samples are then resuspended in 4 µl of an 80% formanide loading dye containing 1×TBE, bromphenol blue and xylene cyanol, heated to 90° C. for 2 minutes, and loaded on 6% polyacrylamde-urea sequencing gels.

Test compounds that do not inhibit production of native RANTES gene product will have the same banding pattern as those of activated PBL and HUT78 cells. Test compounds that inhibit production of native RANTES gene product will have banding patterns matching the noxtract control lane and the negative control Jurkat cells.

Methylation Interference

Methylation interference was assayed according to the protocol of Baldwin (Ausubel, F. M., et al., Green Publishing Associates and Wiley-Interscience, New York (1987)). Preparative EMSA (10-fold scale up of reaction described above) was performed using the C region SacI-to-BspEI single-end-$^{32}$P-labeled restriction fragment. The fragment was labeled with the Klenow fragment. DNA was eluted from the excised bands representing EMSA complexes by electroelution in a Bio-Rad apparatus. Following piperidine cleavage, the DNA ladders were analyzed on standard 10% polyacrylamide-urea sequencing gels (Ausubel, F. M., et al, Green Publishing Associates and Wiley-Interscience, New York (1987)).

UV Cross-linkin Analysis

Preparatve EMSA was performed exactly as described by methylation interference. Before autoradiography, the gel was exposed to UV light (2,500 ml) in a Strane (Stratagene, La Jolla, Calif.) as described previously (Kelsumi, H. M., et al., Mol. Cell. Biol. 13:6690–6701 (1993)). Bands were excised and heated to 70° C. in Laemmli sample buffer. Gel slices were then loaded into the walls of a sodium dodecyl sulfate10% polyacrylamide electophoresis (SDS-10% PAGE) gel run in glycine-SDS buffer (Ausubel, F. M., et al, Green Publishing Associates and Wiley-Interscience, New York (1987)). Molecular weight standards were $^{14}$C-labeled Rainbow markers (Amersham).

EXAMPLE 1

Obtaining the R(A) Binding Site

The R(A) oligonucleotide sequence as well as all other oligonucleotides used in the following examples were synthesized by Genset (San Diego, Calif.) with Xho I, Sal I, Xba I or Nhe I overhangs to allow end-labeling, as described by Ausubel et al., 1987 *In Current Protocols in Molecular Biology* (Green Publishing Assouates and Wiley-lnteseience, New York) p12.2.1, and for ligating into the cloning sites of desired plasmids.

EXAMPLE 2

The R(A) Sequence Function as Enhancers for Heterologous Promoters

An enhancer activity assay was performed to show that the R(A) sequences could function as enhancers for heterologous promoters. This procedure consists of placing between one and three copies of the desired test sequence in front of a minimal promoter and then assaying the results as fold increase in activation as compared to the enhancerless control construct.

Figure 4:
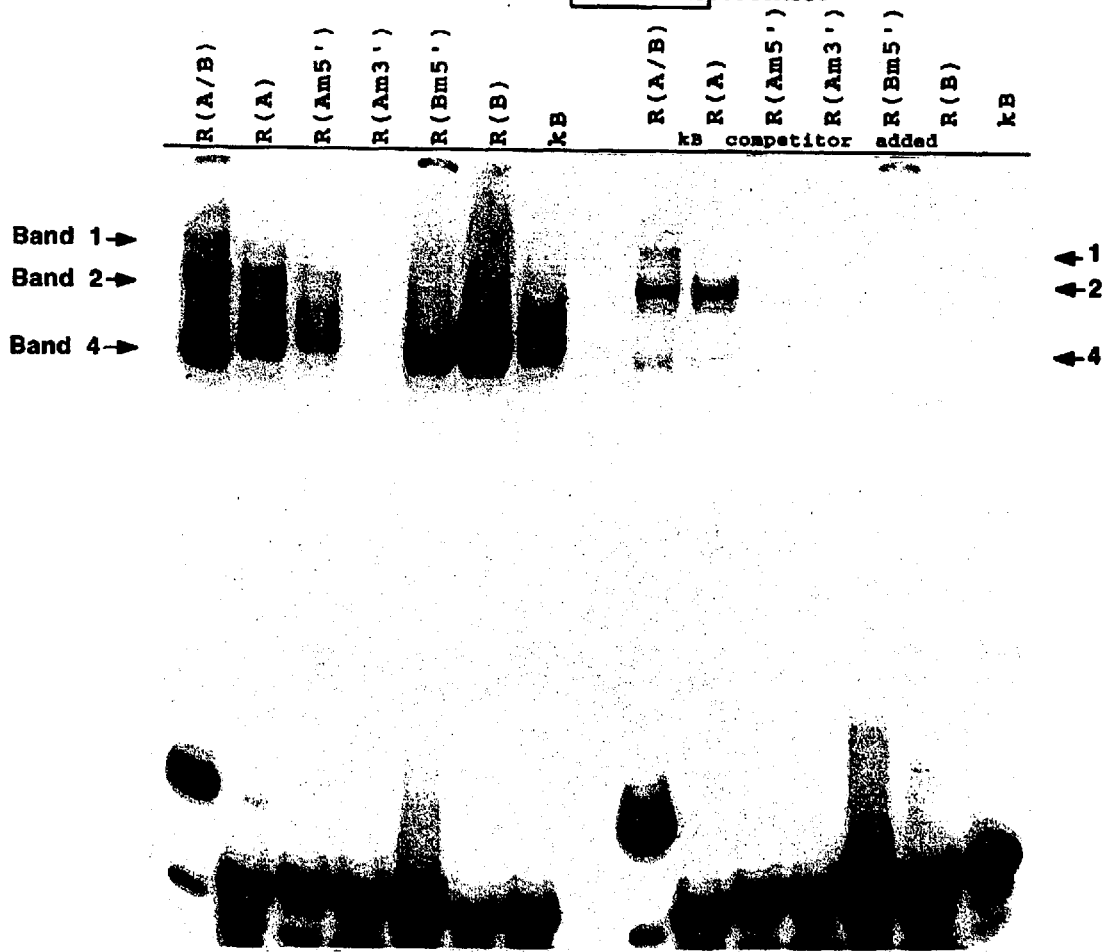
FIG. 4: A series of truncated oligomers derived from the R(A/B) region were used to map the binding patterns seen on EMSA in day 7 PHA stimulated PBL nuclear extract. The right side of the autoradiogram represents a parallel experiment performed in the presence of a 1000 fold molar excess of cold kB (IgkB) competing oligomer. The upper portion of FIG. 4 provides the following sequences: −2 to −76 of the RANTES promoter (SEQ ID NO:22) and its complement (SEQ ID NO:23); R(A/B) (SEQ ID NO:1 and the complementary sequence SEQ ID NO:24); R(A) (SEQ ID NO:10 and the complementary sequence SEQ ID NO:25); R(Am5') (SEQ ID NO:11 and the complementary sequence SEQ ID NO:26); R(Am3') SEQ ID NO:12 and the complementary sequence SEQ ID NO:27); R(B5') (SEQ ID NO:13 and the complementary sequence SEQ ID NO:28); R(B) (SEQ ID NO:14 and the complementary sequence SEQ DI NO:29); and kB (SEQ ID NO:15 and the complementary sequence SEQ ID NO:30).

This enhancer activity assay uses the pGL-2 Promoter vector (Promega, Madison, Wis.) which contains an enhancerless minimal SV40 promoter upstream of the luciferase gene. DNA fragments containing enhancer sequences generally will increase transcription when inserted into this vector either upstream or downstream of the luciferase gene, and in either orientation. FIG. 4 shows the DNA sequences tested for transcriptional enhancer activity. The sequences used in this assay are designated R(A/B), R(A) and R(Am3'). These were generated as synthetic oligomers and cloned as monomers and trimers into either the Xho I or Nhe I sites of the pGL-2 Promoter vector and sequenced to detemiine orientation. These test constructs, along with the control pGL-2 Promoter vector lacking inserts, were then transfected into PHA activated PBL cells and Hut78 cells followed by luciferase reporter gene assays.

Suspension cell cultures of activated PBL cells and Hut78 cells were transfected by electroporation using a BRL Cell-Porator electroporation apparatus according to the manufacturer's specifications for transfection of eukaryotic cells. Briefly, suspension cultures were gently pelleted, and resuspended at $2.0 \times 10^7$ cells/ml in electroporatior media. A cytomegalovirus promoter/enhancer-luciferase fusion construct was used to determine optimal el on voltages (220 V for Hut78 and on average 235 V for activated PBL that had been stimulated with PHA-P (5 $\mu$g/ml) for 1.5 days) at a capacitance of 1180 $\mu$F. Following electrapomtion, the cells were gently resuspended in 4 ml of supplemented RPMI 1640 media containing 20% fetal calf serum and placed in 6 well plates (Falcon, Lincoln Park, N.J.). Approximately 36 hours later, luciferase activity was determined using the Luciferase Assay System Kit (Promega, Madison, Wis.) as described in Nelson et al, *J. Immunol.* 151:2601 (1993).

Figures 5, 6:
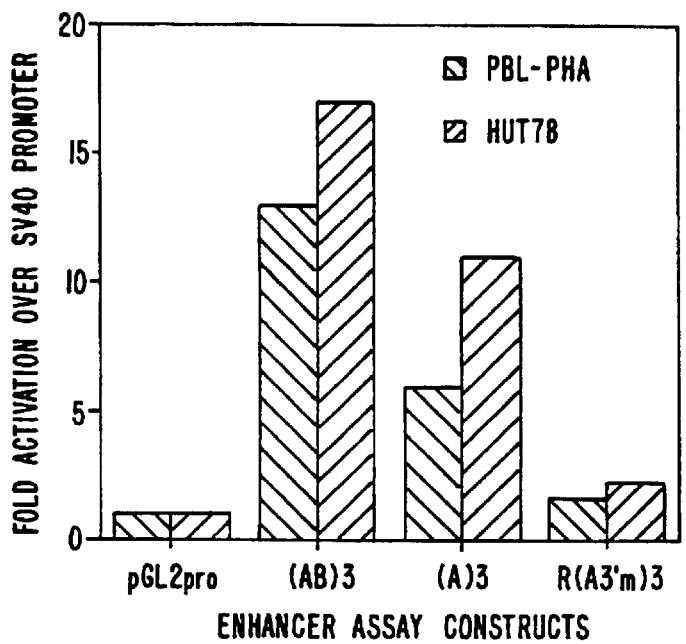
FIG. 5: The R(A/B) and R(A) promoter sequences were assayed as trimers in enhancer assays. Results are averages of quadruplicates for Hut78 cells and triplicates for PBL cells and are presented as fold enhancement over pGL-2 pro (SV40 basal promoter). Baseline values for pGL-2 pro were 262+/−64 for Hut78 cells and 89+/−33 for PBL cells.
FIG. 6: DNA sequence comparison of the murine (SEQ ID NO:16) and human (SEQ ID NO:17) RANTES promoter regions demonstrate conservation of the R(A) enhancer region.
Figures 7A, 7B, 7C:
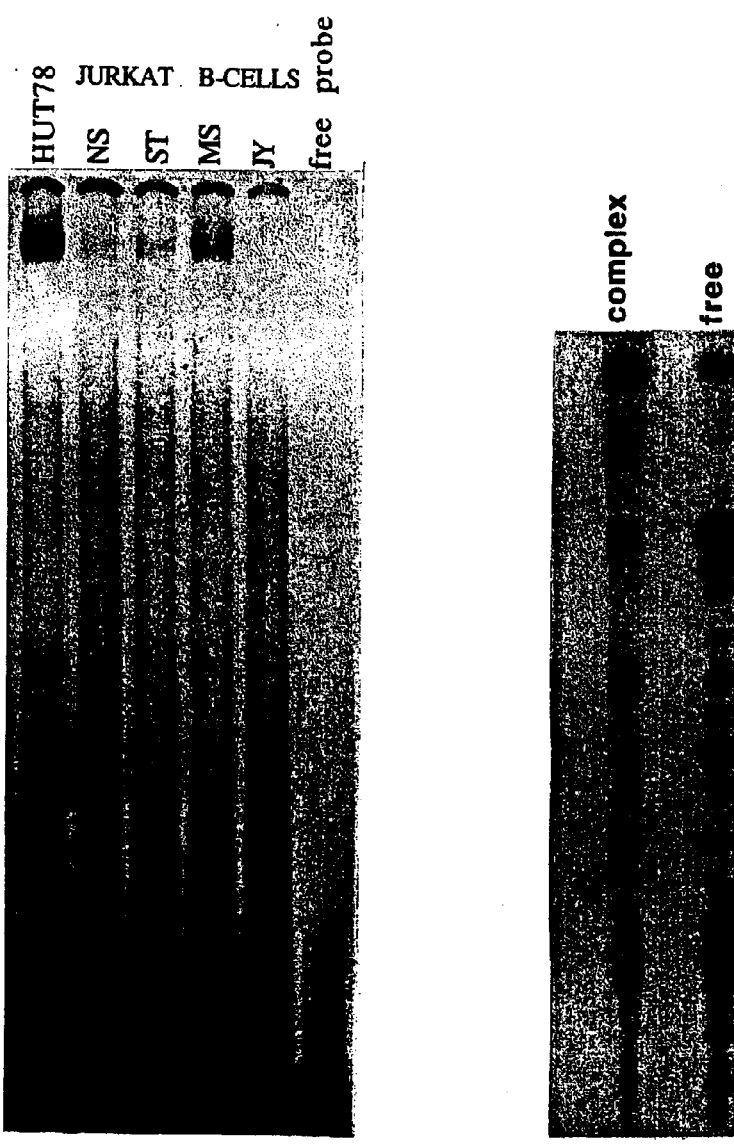
FIGS. 7A–7C: Definition of the binding size for nuclear factors recognizing region C (A) EMSA using $^{32}$P-labeled restriction fragment containing region C. The arrow indicates the major complex. Jurkat T cells were stimulated with 20 ng of PMA per ml and 2 μM ionomycin for 2 h. (B) Methylation interference assay using the same restriction fragment. Undermethylated G residues (contact residues) are indicated by asterisks. Complex, bound probe; free, unbound probe. (C) Comparison of human (SEQ ID NO:3) and murine (SEQ ID NO:18) RANTES promoters at the binding site. Asterisks indicate contact residues. The 5' border nucleotide positions are −187 (human) and −169 (murine) relative to the transcription start site. (+1).

The results, as shown in FIG. 5, are presented as fold activity over the SV40 enhancerless pGL-2 Promoter lacking any inserts. rants were normalized for total protein added to the luciferase reagent (Bio-Rad Bradford protein assay reagent, Bio-Rad, Hercules, Calif.) and are representative data from four to ten separate assays. The R(A/B) trimer produced a twelve to fifteen fold increase in activation and the R(A) trimer produced a 7 to 11 fold increase. These results demonstrate that both R(A/B) and R(A) function as enhancers when placed in front of a heterologous promoter.

EXAMPLE 3

Assays to Test Compounds for Their Potential Inhibitory Effect on the Production of Native Rantes Gene Product The RANTES promoter sequence R(A/B)-luciferase gene fusion assay, DNase I footprinting assay and electrophoretic mobility shift assay (EMSA) are three methods for readily identifying compounds that will inhibit the production of native RANTES gene product. By performing the same assays as described here, but in the presence of a potential inhibitory test compound d, one can readily determine that compound's effect on the production of native RANTES gene product. If the results of assays done in the presence of the test compound are similar to those described below, then the test compound does not have the desired inhibitory effect.

RANTES Promoter Sequence R(A/B)-luciferase Gene Fusion Assay

A 5' to 3' restriction enzyme deletion of the native RANTES promoter left a DNA fragment representing the 192 nucleotides immediately upstream of the transcriptional start site and the complete RANTES 5' untranslated region to the ATG translaional start site. This fragment is designated deletion construct -192 in FIG. 1. This fragment was sufficient for maximal expression of the luciferase reporter gene in both the Hut78 cell line and in day three PHA activated PBL cells. This fragment was subcloned into pSKII bluescript (Stratagene, La Jolla, Calif.), then removed via BssH II digestion and subcloned into the Mlu I site of the pGL-2 Basic luciferase reporter gene plasmid (Promega, Madison, Wis.). Unlike the pGL-2 Promoter, the pGL-2 Basic vector lack eukaryotic promoter and enhancer sequences. The resultant constructs were DNA sequenced to determine orientation.

This construct was then transiently transfected (via electroporation as described in Example 2) into activated PBL cells and rut78 cells. The PBL cells were transfected 36 to 48 hours after activation. Luciferase activity was determined for both cell types approximately 36 hours after transfection using the assay described in Example 2.

The test compound can be added directly to the cell growth media following transfection and results can be compared against results from assays lacking the compound. If a compound inhibits the activation of the R(A/B) site then a corresponding drop in luciferase activity should occur.

DNase I footprinting and EMSA can further confirm the inhibitory effect of the test compound. Both assays can be carried out with either day five activated PBL cells (activated as described in Example 2) or Hut78 cells. For assays performed with PBL cells, the test compound can be added to the cell growth media 1 to 2 days prior to and throughout the activation period. For assays performed with Hut78 cells, the test compound can be added to the cell growth media 1 to 2 days prior to harvesting the nuclear extract.

Figure 3:
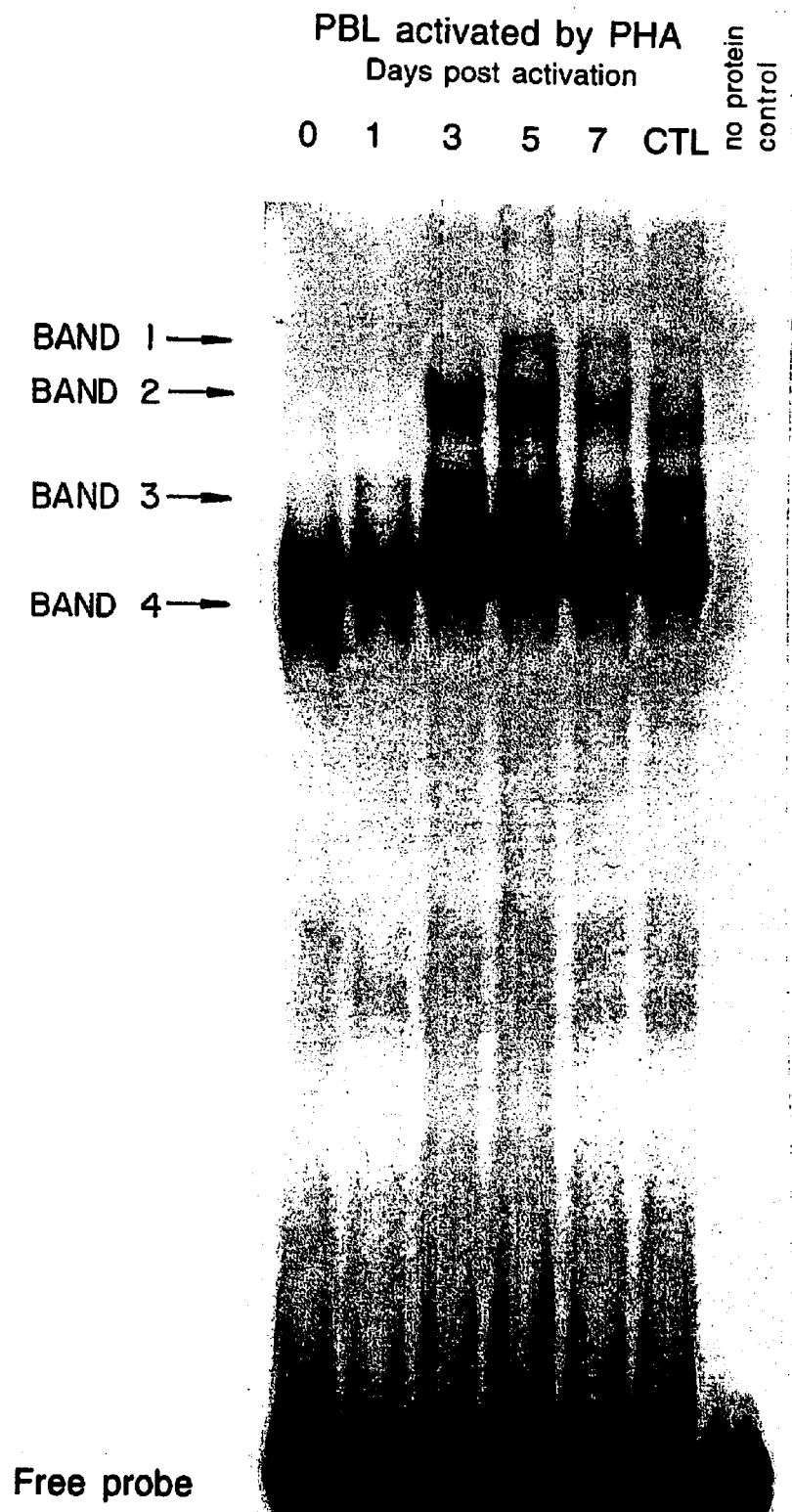
FIG. 3: Electrophoretic mobility shift assay (EMSA) performed using a oligonucleotide probe representing the DNase I footprint identified in FIG. 2 (R(A/B): TCGAGC- TATTTTGGAAACTCCCCTTAGGGGATGCCCCTC AACTGCTCGA (SEQ ID NO:1). A series of nuclear extracts derived from resting PBL cells, and from days 1, 3, 5 and 7 after activation with PHA, as well as from an established CTL line stimulated by alloantigen and conditioned media were used.

Nuclear extracts isolated from resting PBL cells, and from PBL cells following 1, 3, 5, and 7 days of activation with PHA, were used in the EMSA. A series of complexes (labeled bands 1 through 4 in FIG. 3) were found to associate with the R(A) oligonucleotide. The nuclear factor(s) comprising band 4 appear to be constitutively expressed in T cells. The complexes which yield bands 1, 2 and 3 were induced in PBL following PHA activation. Band 3 is seen by day 1 and is variably present in all subsequent time points. The factors responsible for band 2 result in a broad complex on EMSA and were seen by day 3. Band 1 appears last, between days 3 and 5. Of interest, bands 1 and 2 temporally correlate with the induction of RANTES mRNA expression seen following alloantigen or PHA activation of resting peripheral blood T cells. If the test compound inhibits production of native RANTES gene product, band 1 and most of band 2 will not be present.

DNAse I Footprinting Assay

Figure 2:
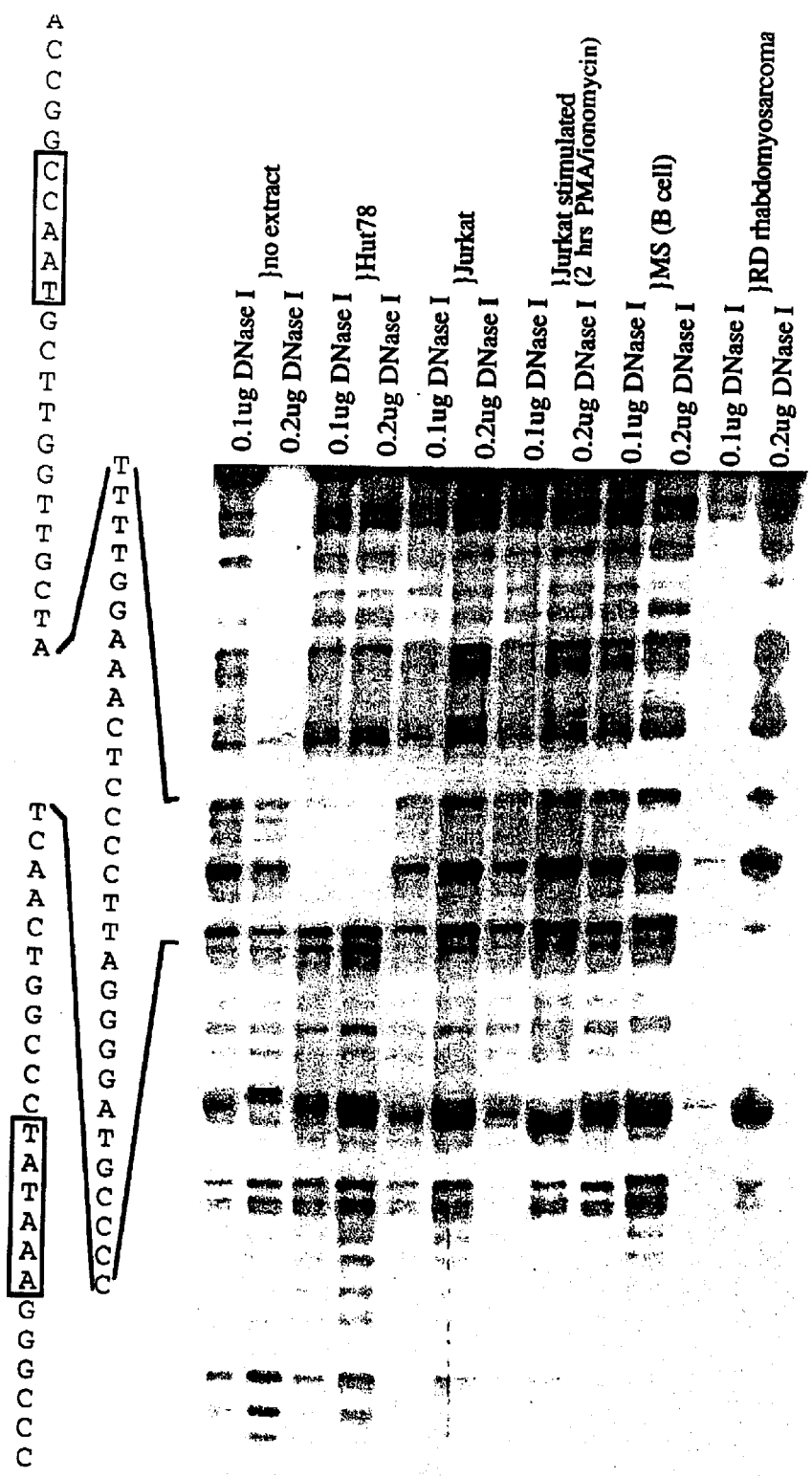
FIG. 2: Binding of nuclear factors to the immediate 192 nucleotides of the RANTES promoter region was tested using DNase I footprint assay. Nuclear extracts isolated from the "late" T cell line Hut78 protected a region from −39 to −75 from DNase I digestion. Nuclear extracts isolated from Jurkat, activated Jurkat (2 hours with PMA (25 μng/ml) plus ionomycin (1 μM)), MS and RD did not protect this region. The sequence of −8 to −79 of the RANTES promoter is shown (SEQ ID NO:21).

DNase I footprinting is used to asy for DNA sequences which could be protected from DNase I digestion by nuclear extracts isolated from activated T cells. DNase I footprinting of the minimal RANTES promoter identifies a large region protected by T cell derived nuclear extracts Nelson et al., 1993 *J. Immunol.* 151:2601) (FIG. 2). The presence of an inhibitory compound will prevent the activated PBL or Hut78 cell nuclear extract from protecting this region. A negative and positive control run on either side of the test compound will produce adequate points of reference.

DNAse I footprinting is performed using a derivation of the procedures described by Durand et al., *Mol Cell. Biol.* 8:1715 (1988) and Jones et al., *Cell* 42:5593 (1985). Binding reactions are carried out under the conditions described above for EMSA but scaled up to 50 μl. After binding, using 50 μg nuclear extracts, 50 μl of a 10 mM $MgCl_2$/5 mM $CaCl_2$ solution is added and 2 μl of an appropriate DNAse I (Worthington, Freehold, N.J.) dilution is added and incubated for 1 minute on ice. DNase I digestion is stopped by adding 90 μl of stop buffer (20 mM EDTA, 1% SDS, 0.2 M NaCl). After addition of 20 μg yeast tRNA as carrier, the samples are extracted two times with an equal volume of phenol/chloroform (1:1) and precipitated after adjusting the solution to 0.3 M sodium acetate and 70% ethanol. DNA samples are then resuspended in 4 μl of an 80% formamide loading dye containing 1×TBE, bromphenol blue and xylene cyanol, heated to 90° C. for 2 minutes, and loaded on 6% polyacrylamide-urea sequencing gels.

Test compounds that do not inhibit production of native RANTES gene product will have the same banding pattern as those of activated PBL and Hut78 cells in FIG. 2. Test compounds that inhibit production of native RANTES gene product will have banding patterns matching the no-extract control lane and the negative control Jurkat lane of FIG. 2.

EXAMPLE 4

Nuclear Factors that Interact with the C Regions

Using the methodologies taught above, we have identified nuclear binding factors that complex with the R(C) region. The transcription factor complex, R(C)FLAT, activates the RANTES promoter through a purine-rich R(C) site. This factor is induced between days 3 and 5 after initial T-cell activation, coincident with the late upregulation of RANTES mRNA. This complex contains at least two DNA binding subunits and does not appear to be related to several transcription factor families known to bind purine-rich sequences. Although R(C)FLAT is highly expressed in many lymphoid cell lines, R(C)FLAT expression does not perfectly correlate with RANTES mRNA expression. The R(C) FLAT-positive cell lines Jurkat, PEER, MS, and Daudi do not express RANTES. Therefore, this transcription factor is not an absolute determinant of RANTES gene expression. Preliminary data indicate that transcriptional regulation through the R(C) site may be context dependent. Neither the R(C) site nor region C were capable of trans-activating a heterologous simian virus 40 basal promoter (data not shown). This is also a property of the T-cell receptor beta enhancer which is much more efficient at transactivating its own promoter than a heterologous one. In addition, it is reminiscent of the context-dependent transcriptional regulatory protein lymphoid enhancer factor 1 whose binding site is found in the T-cell receptor alpha enhancer. Since lymphoid enhancer factor 1 is expressed early in T-lymphocyte ontogeny, it is unlikely to be R(C)FLAT.

Figure 8:
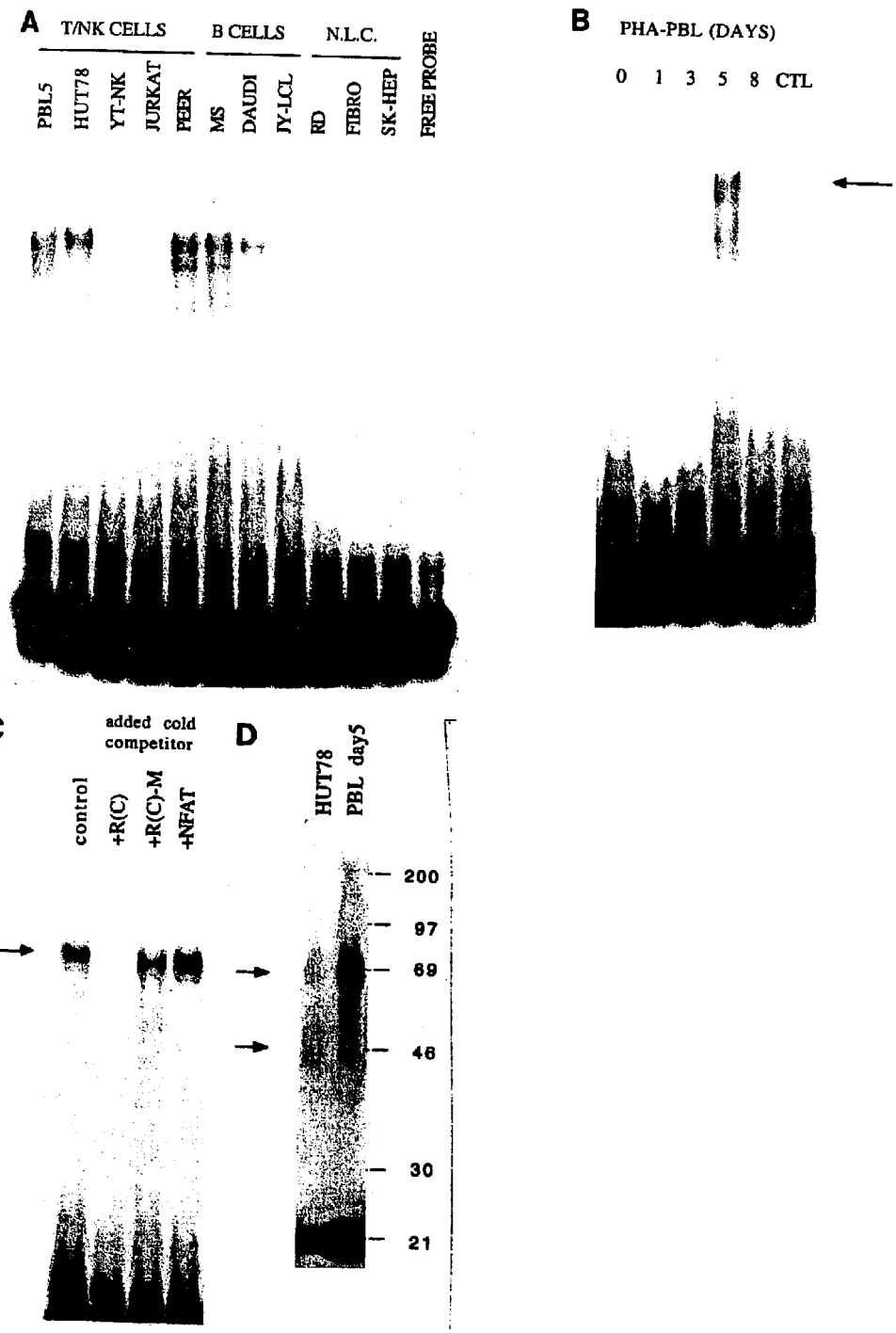
FIGS. 8A–8D: Characterization of the R(C) binding complex. (8A) EMSA using 32P-labeled R(C) oligonucleotide probe and nuclear extracts from the indicated cell lines. The arrow points to the major complex. Fibro, normal human dermal fibroblasts. (8B) EMSA using the same probe described for panel A and nuclear extracts prepared at the indicated time points in a peripheral blood T-cell activation time course. CTL, healthy human cytolytic T-cell line. (8C) R(C) size recognition by HUT78-derived nuclear proteins is sequence specific. Cold competition EMSA using labeled R(C) site oligonucleotide and unlabeled excess oligonucleotides as indicated. The NFAT sequence is from the human IL-2 promoter (GATCGGAGGAAAAACTGT TCATACAGAAGGCGTGATC) (SEQ ID NO:6). (8D) UV cross-linking analysis of factors bound to the R(C) oligonucleotide in 5-day PHA-treated PBL and HUT78 T cells. The positions of the molecular mass markers (in kilodaltons) are indicated on the right. Arrows point to reproducibly cross-linked products.

FIG. 8 provides the characterization of the R(C) binding complex using EMSA. It appears that R(C) has an apparently novel complex with at least two DNA binding subunits.

PBL from healthy human donors were activated with the T-cell mitogen PHA to mimic antigen activation. Nuclear extracts were isolated at time zero and 1, 3, 5, and 8 days following activation. The R(C) site binding complex was strongly, but transiently, upregulated between days 3 and 5 (FIG. 8B). Additional time course experiments have shown that levels of this complex remain high at least through days 4 to 6 (data not shown). These kinetics are unusual since induction of most known transcription factors occurs within the first 24 h after T-cell activation (46). The timing of R(C) complex upregulation is coincident with the late upregulation of RANTES mRNA in normal T cells. The complex is named R(C)FLAT for RANTES C site binding factor of late-activated T cells.

R(C)FLAT is composed of at least two DNA binding subunits. In order to characterize the components of the R(C)FLAT complex, competition assays were performed using excess cold oligonucleotides representing known purine-rich transcription factor binding sites. R(C) binding activity was specifically inhibited by the homologous oligonucleotide but not the mutant R(C)-M oligonucleotide nor the purine-rich NFAT site of the human IL-2 promoter (FIG. 8C). Further, the binding detected in the other R(C) complex-positive cell types was similarly found to be sequence-specific by competition assay (data not shown). R(C) binding was not inhibited by using consensus binding sites for AP-1, NPkB, C/EBP, NFIL6, Oct-1, or ets family transcription factors (data not shown).

To further characterize the DNA binding subunits of R(C) FLA^\T, the complex was resolved on EMSA and subjected to UV cross-linking as described in Mol. Cell Biol 13:6690–6701 using 2500 mJ in a stratolinker from Stratagene.

After exposure to X-ray film, the EMSA complex band was excised. Bands were run on an SDS-PAGE 10% gel in a Tris-Glycine-SDS buffer (FIG. 8D). Two proteins which migrated at approximately 65 and 45 kDa were reproducibly crosslinked to the R(C) site. Subtracting the mass of the cross-linked DNA (17 kDa), the proteins have apparent molecular masses of approximately 48 and 28 kDa, respectively. These cross-lined products were found in both HUT78 T-cells and in 5-day PHA-activated PBL.

R(C) site binding activity is widespread but highly expressed in lymphoid cell lines. Nuclear extracts prepared from cell lines of various lineages was tested for R(C) site binding protein activity (FIG. 8A). High levels of R(C) complex activity were found in normal PBL activated with PHA for 5 days, the lymphoid tumor cell lines HUT78, PEER (a γδ leukemia T cell line), and two Burkitt's lymphoma (B-cell) lines, MS and Daudi. Intermediate levels of expression were found in Jurkat and YT7C2 (natural killer tumor cel line). Jurkat, a T-cell leukemia line with a resting phenotype, expressed it at a much lower level. Levels of this complex were not altered by stimulation of Jurkat for 2 h with the phorbol ester phorbol myristate acetate (PMA) and ionomycin under conditions known to upregulate transcription factors such as NFAT, NPkB, and AP-1. Expression was low to undetectable in a third B cell line, JY, and the nonlymphoid cell lines RD, a rhabdomyosarcoma (muscle cell) line, normal human dermal fibroblasts, and the endothelial cell tumor line SK-HEP. Binding activity was also detected in U937, a monocytic cell line, and in HepG2, a hepatoma cell line (data not shown). An additional band, which migrated slightly faster in EMSA, was found in the MS and PEER lanes. This binding activity varied among experiments and may be that of an R(C) binding complex degradation product.

EXAMPLE 5

Nuclear Factors that Interact with the Rantes E Regions

Nuclear Factors Bind to Region E

Figure 9:
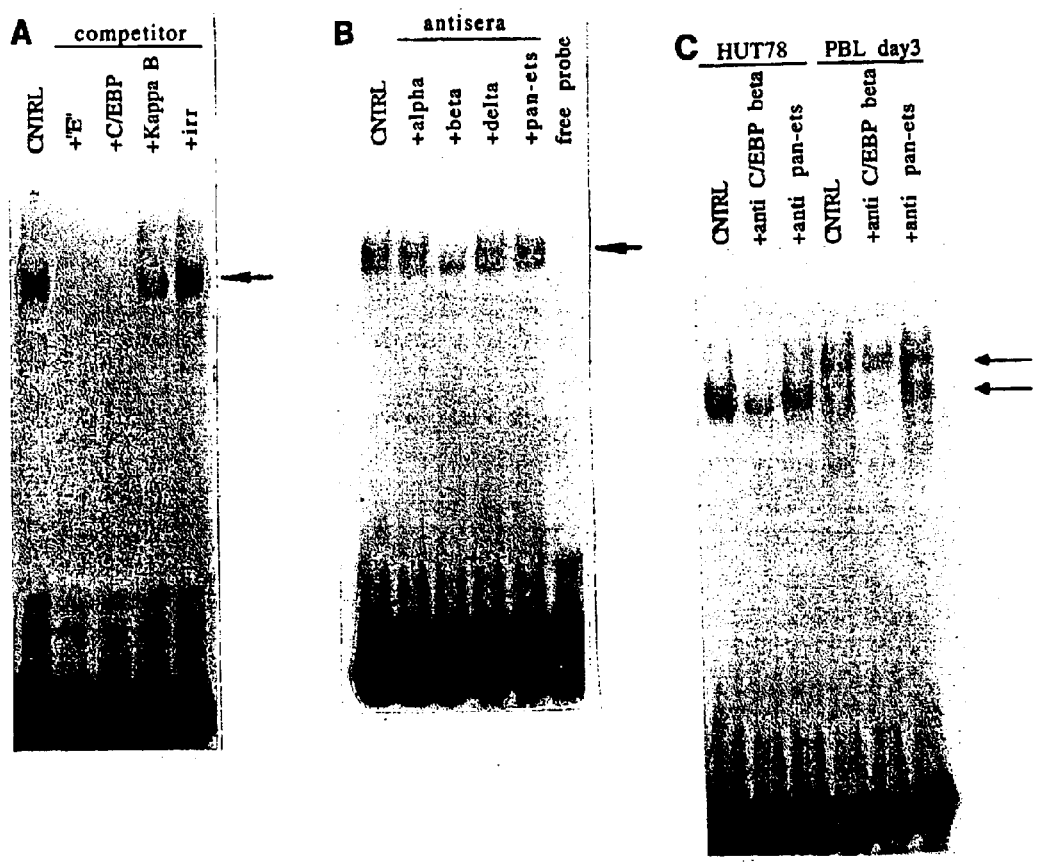
FIGS. 9A–9C: The region E binding complex contains NFIL6/C/EBPβ. (9A) EMSA using $^{32}$P-labeled region E oligonucleotide and HUT78 nuclear extract. Cold oligonucleotide competitors were used in 1,000-fold molar excess. "E," homologous oligonucleotide; C/EBP, C/EBP consensus binding site (Santa Cruz Biotech catalog no. so-2525); Kappa B, NF-κB binding sequence from immunoglobulin kappa light-chain enhancer (TCGAGTCAGAGGGGACTTTCCGAGTCGA) (SEQ ID NO: 7) (49); irr, irrelevant sequence oligonucleotide (GATCCTGGAAGGGAGAGTGGAGATC) (SEQ ID NO:8). (9B) EMSA-antibody supershift/blocking assay using the probe and extracts described for panel A. Rabbit polyclonal immunoglobulin G (1 μg) was added as described in Materials and Methods. Alpha, beta, and delta refer to the specific C/EBP family members against which the antisera are directed (Santa Cruz Biotech). The arrow points to the blocked EMSA complex. (9C) Similar to the assay described for panel B but with nuclear extracts from both HUT78 T-cells and PBL 3 days after PHA treatment. Antisera were added as indicated. The lower arrow points to the C/EBPβ/ NFIL6 complex. The upper arrow indicates the additional late PBL-derived EMSA complex CNTRL control.

FIG. 9 provides evidence of a nuclear factor binding to R(E) using EMSA. Nuclear factors binding to Region E were also identified by cold oligonucleotide competition and antibody supershift/blocking assays. HUT78-derived nuclear factors interacting with a region B oligonucleotide, which includes the region of NFIL6 binding site homology, formed a doublet of complex binds on EMSA (FIG. 9A). This doublet was specifically inhibited by an excess of cold homologous competitor oligonucleotide or consensus C/EBP binding site oligonucleotide. A kappa B site and another irrelevant oligonucleotide were not able to inhibit this complex.

To determine if these complexes were formed by C/EBP family proteins, supershift/blocking antisera against C/EBPα, C/EBPβ/NFIL6, and C/EBPδ/NFIL6β were tested to identify the complex (FIG. 9B). Only the C/EBPβ/NFIL6 antiserum affected the binding pattern by preventing the formation of the upper complex of the doublet. A control antiserum to ets family proteins had not effect on the EMSA pattern. To confirm the presence of NFIL6 in normal T cells, extras from day-3 PHA-activated PBL were tested in the supershift assay alongside the HUT78 nuclear extracts (FIG. 9C). The activated PBL proteins formed a doublet similar to, but less distinct than, that found in HUT78. Furthermore, this complex was also blocked by the C/EBPβ/NFIL6 antiserum. An additional upper band was found in the activated PBL EMSA pattern but not in the HUT78 lanes. This complex was not affected by the C/EBPβ/NFIL6 antiserum. Antibodies of C/EBPα and C/EBPδ did not affect the activated PBL-derived EMSA pattern (data not shown).

Cotransfection/reporter Gene Assays with C/EBPβ/NFIL6 Expression Vector

To confirm that NFIL6 could activate transcription through region E, an expression vector containing the NFIL6 cDNA under control of the elongation factor promoter was cotransfected with the RANTES –195 promoter-luciferase construct. The parent expression vector without the cDNA was used as a control. The NFIL6 cDNA stimulated RANTES promoter driven activity over six-fold in HUT78 T-cells. Activity from a reporter construct with region E internally deleted was only minimally enhanced by the NFIL6 expression vector.

Figure 10:
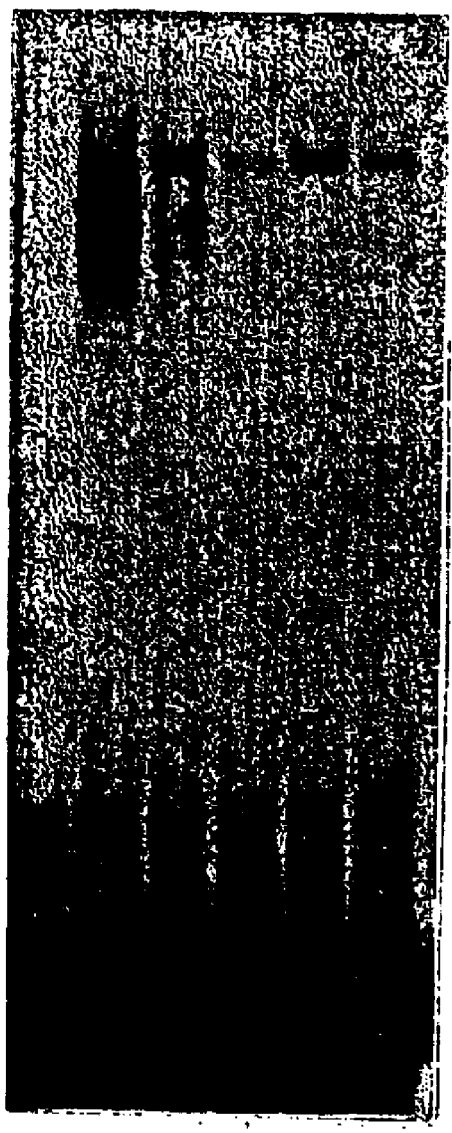
FIG. 10: EMSA using $^{32}$P-labeled region E oligonucleotide and the same extracts described in the description to FIG. 8B. "E" region FLAT denotes the 1at PBL-derived EMSA complex. The NFIL6 arrow indicates the complex C/EBPβ/NFIL6 as determined by the antibody blocking assay.

By using the same nuclear extracts as those used for the experiment shown in FIG. 8B, the kinetics of NFIL6 induction in activated T cells were examined. Unlike the R(C) FLAT complex, the NFIL6 complex is upregulated by day 1 of the time course and is nearly absent by day 5. The upper band formed by PBL nuclear extracts was upregulated later, by day 3, and was maintained throughout the remainder of the time course. It was also present in terminally differentiated normal cytotoxic T cells (FIG. 10). We refer to this as the E region binding FLAT.

We have identified another late-activated transcription factor complex, R(A)FLAT which acts through a downstream kappa-B-like site. R(C)FLAT and R(A)FLAT mediate transcriptional control mechanisms likely to contribute to late upregulation of RANTES mRNA in normal T cells. In addition, the E region binding FLAT complex may also play a role in this process. It is also upregulated on day 3 of T-cell activation and is maintained by fully differentiated cytotoxic T cells, which express RANTES constitutively. Formal demonstration of its role in RANTES gene expression, however, awaits further characterization of the proteins forming this EMSA complex.

CONCLUSION

Figure 11:
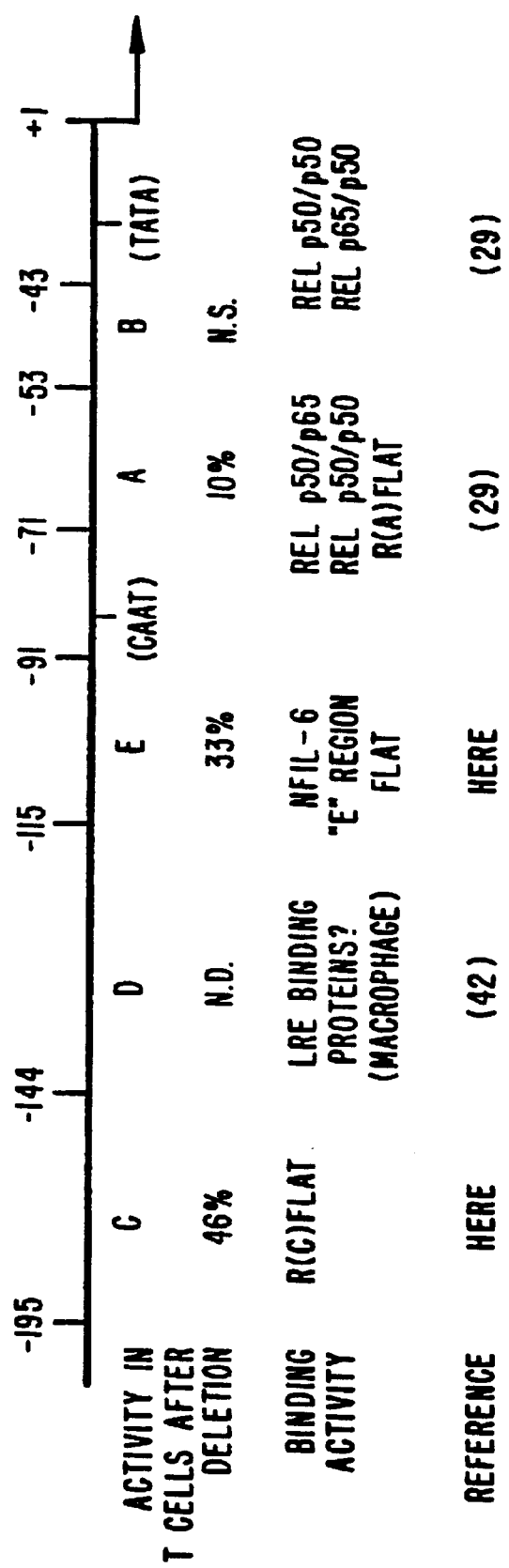
FIG. 11: Diagram of the regulatory regions identified in the −195 RANTES promoter and their positions relative to the transcription start site +1. The percentages of activity in T cells after the deletions relative to the −195 wild-type activity and are averages derived from the number of experiments per region: for C, n=14, for E, n=7 and for A, n=4. The binding activities identified within regions are also listed N.D., not determined; N.S. not significantly altered.

In identifying two additional functional regions of the RANTES promoter, there are now four identified cis-acting elements contributing to RANTES transcription in various systems. Regions A through E (FIG. 11) comprise a promoter with the capacity to response to different microenvironmental and developmental stimuli. Region A binds proteins of the Rel family and the late-activated R(A)FLAT complex. Region B was not found to contribute significantly to activity in T cells but can also bind members of the Rel family. Region C contains a purine-rich sequence that binds the R(C)FLAT complex. Region D, highly conserved between murine and human promoters, contains sequences described as a lipopolysaccharide-responsive element in murine macrophages. Finally, region E, also described here, binds the well-characterized NFIL6 transcription factor and another, as yet uncharacterized, late-activated factor in normal T cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid sequence selected from the group consisting of: region A having SEQ ID NO:2; binding site C having SEQ ID NO:3 GATGAGAGAGCAGT; Region C having SEQ ID NO:4 GAGCTCACTCTAGAT-GAGAGAGCAGTGAGGGAGAGACA-GAGACTCGAATTT; and region E having SEQ ID NO:5 TTTGTGCAATTTCACTTATGATACC, wherein said nucleic acid sequence, when operably linked to a minimal promoter and a heterologous nucleic acid molecule to form an expression cassette, induces expression of said heterologous nucleic acid molecule when the expression cassette is transfected into a peripheral blood lymphocyte and said transfected lymphocyte is activated with an anti-CD3 antibody or a mitogen.

2. A method for inducing the expression of a heterologous protein in a host cell comprising:
   a) introducing into a host cell an expression cassette comprising a heterologous nucleic acid sequence encoding a heterologous protein operably linked to a recombinant promoter comprising a human RANTES promoter R(A) enhancer element and a minimal promoter, wherein said recombinant promoter directs expression of the operably linked heterologous nucleic acid sequence when the expression cassette is transfected into a peripheral blood lymphocyte (PBL) and said transfected PBL is contacted with an anti-CD3 antibody, with the proviso that the recombinant promoter does not comprise the native NFκB binding element located between the R(A) enhancer element and the TATA box in the native human RANTES gene; and
   b) inducing expression of the heterologous protein.

3. A method of claim 2, wherein said expression cassette is in a plasmid.

4. A method of claim 2 wherein said heterologous protein is selected from the group consisting of: a hormone, a viral capsid protein, a bacterial enzyme and a mammalian enzyme.

5. A method of claim 2 wherein said nucleic acid sequence is transfected into a human host cell.

6. A method of claim 2, wherein the host cell is induced to express the heterologous nucleic acid sequence encoding the heterologous protein by contacting the cell with an appropriate activator in an amount sufficient to induce expression of the heterologous nucleic acid sequence.

7. A method of claim 2 wherein the host cell is selected from the group consisting of activated peripheral blood lymphocytes and T cell tumor line Hut78.

8. A method of claim 2, wherein the R(A) enhancer element is operably linked to the R(C) binding site located −182 to −169 relative to the RANTES transcription start site of the human RANTES promoter or to the Region "C" sequence located −195 to −144 relative to the RANTES transcription start site of the human RANTES promoter.

9. A method of claim 2, wherein the R(A) enhancer element is operably linked to the Region E sequence located −115 to −91 relative to the RANTES transcription start site of the human RANTES promoter.

10. The method according to claim 2, wherein the host cell is a peripheral blood lymphocyte, and wherein said inducing comprises contacting said lymphocyte with a mitogen.

11. The method according to claim 2, wherein the host cell is a T lymphocyte, and wherein said inducing comprises contacting said lymphocyte with a mitogen.

* * * * *

SEQUENCE LISTING

<160> NUMBER OF SEQ ID NOS: 30

<210> SEQ ID NO 1
<211> LENGTH: 49
<212> TYPE: DNA
<213> ORGANISM: Homo sapiens

<400> SEQUENCE: 1
tcgagctatt ttggaaactc cccttagggg atgcccctca actgctcga        49

<210> SEQ ID NO 2

```
<211> LENGTH: 23
<212> TYPE: DNA
<213> ORGANISM: Homo sapiens

<400> SEQUENCE: 2
gctattttgg aaactcccct tag                                              23

<210> SEQ ID NO 3
<211> LENGTH: 14
<212> TYPE: DNA
<213> ORGANISM: Homo sapiens

<400> SEQUENCE: 3
gatgagagag cagt                                                        14

<210> SEQ ID NO 4
<211> LENGTH: 51
<212> TYPE: DNA
<213> ORGANISM: Homo sapiens

<400> SEQUENCE: 4
gagctcactc tagatgagag agcagtgagg gagagacaga gactcgaatt t               51

<210> SEQ ID NO 5
<211> LENGTH: 25
<212> TYPE: DNA
<213> ORGANISM: Homo sapiens

<400> SEQUENCE: 5
tttgtgcaat ttcacttatg atacc                                            25

<210> SEQ ID NO 6
<211> LENGTH: 38
<212> TYPE: DNA
<213> ORGANISM: Homo sapiens

<400> SEQUENCE: 6
gatcggagga aaaactgttt catacagaag gcgtgatc                              38

<210> SEQ ID NO 7
<211> LENGTH: 28
<212> TYPE: DNA
<213> ORGANISM: Homo sapiens

<400> SEQUENCE: 7
tcgagtcaga ggggactttc cgagtcga                                         28

<210> SEQ ID NO 8
<211> LENGTH: 25
<212> TYPE: DNA
<213> ORGANISM: Homo sapiens

<400> SEQUENCE: 8
gatcctggaa gggagagtgg agatc                                            25

<210> SEQ ID NO 9
<211> LENGTH: 10
<212> TYPE: DNA
<213> ORGANISM: Homo sapiens

<400> SEQUENCE: 9
gggactttcc                                                             10
```

```
<210> SEQ ID NO 10
<211> LENGTH: 29
<212> TYPE: DNA
<213> ORGANISM: Artificial Sequence
<220> FEATURE:
<223> OTHER INFORMATION: synthetic oligonucleotides

<400> SEQUENCE: 10
tcgagctatt ttggaaactc ccctttcga                                29

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotides

<400> SEQUENCE: 11
tcgagctcgg aaactcccct tgatcatcga                               30

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotides

<400> SEQUENCE: 12
tcgagctcta ttttggaaac tgatcatcga                               30

<210> SEQ ID NO 13
<211> LENGTH: 34
<212> TYPE: DNA
<213> ORGANISM: Artificial Sequence
<220> FEATURE:
<223> OTHER INFORMATION: synthetic oligonucleotides

<400> SEQUENCE: 13
tcgacccctt agggatgcc cctcaactgc tcga                           34

<210> SEQ ID NO 14
<211> LENGTH: 28
<212> TYPE: DNA
<213> ORGANISM: Artificial Sequence
<220> FEATURE:
<223> OTHER INFORMATION: synthetic oligonucleotides

<400> SEQUENCE: 14
tcgagctagg ggatgcccct cagatcga                                 28

<210> SEQ ID NO 15
<211> LENGTH: 29
<212> TYPE: DNA
<213> ORGANISM: Artificial Sequence
<220> FEATURE:
<223> OTHER INFORMATION: synthetic oligonucleotides

<400> SEQUENCE: 15
tcgagtcaga ggggactttc cgagatcga                                29

<210> SEQ ID NO 16
<211> LENGTH: 56
<212> TYPE: DNA
<213> ORGANISM: Homo Sapiens

<400> SEQUENCE: 16
```

-continued cttggttgct attttggaaa ctccccttag gggatgcccc tcaactgccc tataaa    56

<210> SEQ ID NO 17
<211> LENGTH: 57
<212> TYPE: DNA
<213> ORGANISM: Mus musculus

<400> SEQUENCE: 17
tttggtgtct tttgtggaaa ctccccaagt cctggggcta ccctggctcc ctataaa    57

<210> SEQ ID NO 18
<211> LENGTH: 14
<212> TYPE: DNA
<213> ORGANISM: Mus musculus

<400> SEQUENCE: 18
gactggaggg cagt    14

<210> SEQ ID NO 19
<211> LENGTH: 11
<212> TYPE: DNA
<213> ORGANISM: Homo sapiens

<400> SEQUENCE: 19
ggaaactccc c    11

<210> SEQ ID NO 20
<211> LENGTH: 58
<212> TYPE: DNA
<213> ORGANISM: Homo sapiens

<400> SEQUENCE: 20
cagtgaggga gagacagaga ctcgaatttc cggagctatt tcagttttct tttccgtt    58

<210> SEQ ID NO 21
<211> LENGTH: 74
<212> TYPE: DNA
<213> ORGANISM: Homo sapiens

<400> SEQUENCE: 21
accggccaat gcttggttgc tatttggaa actccccta gggatgccc ctcaactggc    60 cctataaagg gccc    74

<210> SEQ ID NO 22
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 22
ggccaatgct tggttgctat tttggaaact ccccttaggg gatgccctc aactgccta    60 taagggca gcctg    75

<210> SEQ ID NO 23
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 23
ccggttacga accaacgata aaacctttga ggggaatccc catcggggag aagacgggat    60
atttccccgt cggac                                                          75

<210> SEQ ID NO 24
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 24
agctcgataa aacctttgag gggaatcccc tacggggagt tgacgagct                     49

<210> SEQ ID NO 25
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 25
agctcgataa aacctttgag gggaaagct                                           29

<210> SEQ ID NO 26
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 26
agctcgagcc tttgagggga actagtagct                                          30

<210> SEQ ID NO 27
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 27
agctcgagat aaaacctttg actagtagct                                          30

<210> SEQ ID NO 28
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 28
agctggggaa tcccctacgg ggagttgacg agct                                     34

<210> SEQ ID NO 29
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 29
agctcgatcc cctacgggga gtctagct                                            28

<210> SEQ ID NO 30
<211> LENGTH: 30
<212> TYPE: DNA

```
<213> ORGANISM: Artificial Sequence
<220> FEATURE:
<223> OTHER INFORMATION: synthetic oligonucleotide

<400> SEQUENCE: 30
aagctcagtc tcccctgaaa ggctctagct                                    30
```